United States Patent
Tang et al.

(10) Patent No.: US 7,291,602 B2
(45) Date of Patent: *Nov. 6, 2007

(54) 11,12-LACTONE BICYCLOLIDES

(75) Inventors: Datong Tang, Watertown, MA (US); Yonghua Gai, North Grafton, MA (US); Ying Sun, Waltham, MA (US); Zhigang Chen, Acton, MA (US); Yat Sun Or, Watertown, MA (US); Zhe Wang, Hockessin, DE (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/302,529

(22) Filed: Dec. 13, 2005

(65) Prior Publication Data

US 2006/0148731 A1 Jul. 6, 2006

Related U.S. Application Data

(60) Provisional application No. 60/635,702, filed on Dec. 13, 2004.

(51) Int. Cl.
*A61K 31/70* (2006.01)
*C07H 17/08* (2006.01)

(52) U.S. Cl. .................. 514/29; 536/7.2; 536/7.3; 536/7.4

(58) Field of Classification Search .......... 536/7.2, 536/7.3, 7.4; 514/29
See application file for complete search history.

(56) References Cited

U.S. PATENT DOCUMENTS

| 5,866,549 A | 2/1999 | Or et al. |
| 6,075,011 A | 6/2000 | Or et al. |
| 6,740,642 B2 | 5/2004 | Angehr et al. |

FOREIGN PATENT DOCUMENTS

| EP | 0 559 896 A1 | 9/1993 |
| WO | WO 93/21200 | 10/1993 |
| WO | WO 97/10251 | 3/1997 |
| WO | WO 00/78773 A2 | 12/2000 |
| WO | WO 03/095466 A1 | 11/2003 |
| WO | WO 03/097659 A1 | 11/2003 |

OTHER PUBLICATIONS

U.S. Appl. No. 11/008,581, filed Dec. 7, 2004, Or et al.
U.S. Appl. No. 11/324,502, filed Jan. 2, 2006, Or et al.
U.S. Appl. No. 11/236,043, filed Sep. 27, 2005, Or et al.
U.S. Appl. No. 11/302,525, filed Dec. 13, 2005, Tang et al.
Zhenkun, Ma, et al., "Novel Erythromycin Derivatives With Aryl Groups Tethered to the C-6 Position are Potent Protein Synthesis Inhibitors and Active Against Multidrug-Resistant Respiratory Pathogens," *J. Med. Chem.*, 44:4137-4156 (2001).

*Primary Examiner*—Elli Peselev
(74) *Attorney, Agent, or Firm*—Suanne Nakajima; Carolyn S. Elmore; Elmore Patent Law Group

(57) ABSTRACT

The present invention discloses compounds of formula I, or pharmaceutically acceptable salts, esters, or prodrugs thereof:

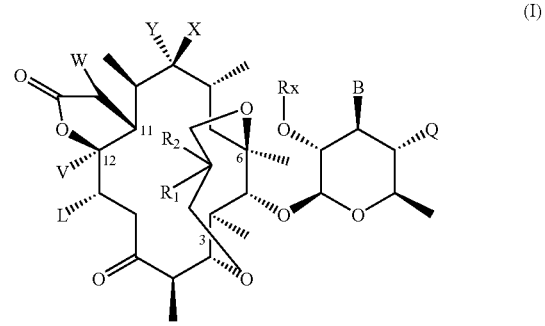

(I)

which exhibit antibacterial properties. The present invention further relates to pharmaceutical compositions comprising the aforementioned compounds for administration to a subject in need of antibiotic treatment. The invention also relates to methods of treating a bacterial infection in a subject by administering a pharmaceutical composition comprising the compounds of the present invention. The invention further includes process by which to make the compounds of the present invention.

23 Claims, No Drawings

11,12-LACTONE BICYCLOLIDES

RELATED APPLICATION

This application claims the benefit of U.S. Provisional Application No. 60/635,702, filed on Dec. 13, 2004. The entire teachings of the above application are incorporated herein by reference.

TECHNICAL FIELD

The present invention relates to novel semisynthetic macrolides having antibacterial activity that are useful in the treatment and prevention of bacterial infections. More particularly, the invention relates to tetracyclic bicyclicolide compounds, compositions containing such compounds and methods for using the same, as well as processes for making such compounds.

BACKGROUND OF THE INVENTION

The spectrum of activity of macrolides, including erythromycin, covers most relevant bacterial species responsible for upper and lower respiratory tract infections. 14-membered ring macrolides are well known for their overall efficacy, safety and lack of serious side effects. Erythromycin however is quickly degraded into inactive products in the acidic medium of the stomach resulting in low bioavailability and gastrointestinal side effects. Improvement of erythromycin pharmacokinetics has been achieved through the synthesis of more acid-stable derivatives, for example, roxithromycin, clarithromycin, and the 15-membered ring macrolide azithromycin. However, all these drugs, including 16-membered ring macrolides, present several drawbacks. They are inactive against $MLS_B$-resistant streptococci ($MLS_B$=Macrolides-Lincosamides-type B Streptogramines) and with the exception of azithromycin, weakly active against *Haemophilus influenzae*. Futhermore, the resistance of *Streptococcus pneumoniae* to erythromycin has increased significantly in recent years (5% to above 40%). There is a high percentage of cross-resistance to penicillin among these isolates, with a worldwide epidemic spread of 10-40% in some areas.

There is, therefore, a clear need for new macrolides that overcome the problem of pneumococcal resistance, have good pharmacokinetic properties and acid stability while continuing to be active against *H. influenzae*. These new macrolides will be ideal candidates for drug development in the first line therapy of upper respiratory tract infections ("URTI") and lower respiratory tract infections ("LRTI").

Kashimura et al. have disclosed 6-O-methylerythromycin derivatives having a tricyclic basic nuclear structure in European Application 559896, published Nov. 11, 1991. Also, Asaka et al. have disclosed 5-O-desoaminylerythronolide derivatives containing a tricyclic carbamate structure in PCT Application WO 93/21200, published Apr. 22, 1992.

Recently erythromycin derivatives containing a variety of substituents at the 6-O position have been disclosed in U.S. Pat. Nos. 5,866,549 and 6,075,011 as well as PCT Application WO00/78773. Furthermore, Ma et. al. have described erythromycin derivatives with aryl groups tethered to the C-6 position in *J. Med. Chem.*, 44, pp 4137-4156 (2001). PCT application WO 97/10251, published Mar. 20, 1997, discloses intermediates useful for preparation of 6-O-methyl 3-descladinose erythromycin derivatives. U.S. Pat. Nos. 5,866,549 and 6,075,011, and PCT application WO 00/78773, published Dec. 28, 2000, disclose certain 6-O-substituted erythromycin derivatives.

PCT Application WO 03/095466 A1, published Nov. 20, 2003 and PCT Application WO 03/097659 A1, published Nov. 27, 2003 disclose a series of bicyclic erythromycin derivatives.

PCT Application WO 02/16380 A1, published Aug. 21, 2003, PCT Application WO 03/072588 A1, published Sep. 3, 2003 and PCT Application WO 2004/016634 A1 disclose a series of C11-C12 lactone erythromycin ketolides.

SUMMARY OF THE INVENTION

The present invention provides a novel class of tetracyclic bicyclolide compounds that possess antibacterial activity.

In one embodiment, the compounds of the present invention are represented by formula I, as illustrated below:

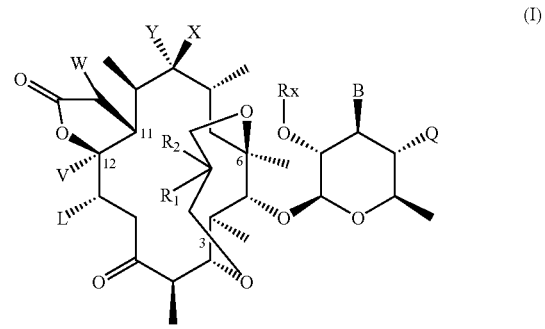

(I)

or the pharmaceutically acceptable salts, esters and prodrugs thereof, wherein W is selected from the group consisting of:
  a) hydrogen
  b) cyano
  c) -E-$R_3$, where E is S, SO, $SO_2$, NH, $NCH_3$, $CH_2O$, $CH_2NH$, $CH_2NCH_3$ or CO, $CO_2$, CONH; and $R_3$ is independently selected from the group consisting of:
    (i) —$C_1$-$C_6$ alkyl, —$C_2$-$C_6$ alkenyl, or —$C_2$-$C_6$ alkynyl; and
    (ii) —$C_1$-$C_6$ substituted alkyl, —$C_2$-$C_6$ substituted alkenyl, or —$C_2$-$C_6$ substituted alkynyl;
  provided that when E=S(O) or $SO_2$, $R_3$ cannot be hydrogen;

$R_1$ is selected from the group consisting of:
  a) hydrogen; deuterium;
  b) —$CH_2OH$;
  c) aryl; substituted aryl;
  d) heteroaryl; substituted heteroaryl;
  e) —$C_1$-$C_6$ alkyl, —$C_2$-$C_6$ alkenyl, or —$C_2$-$C_6$ alkynyl containing 0, 1, 2, or 3 heteroatoms selected from O, S or N, optionally substituted with one or more substituents selected from halogen, aryl, substituted aryl, heteroaryl, or substituted heteroaryl;

$R_2$ is:
  a) hydrogen;
  b) hydroxy;
  c) activated hydroxy;

when $R_1$ is H, $R_2$ is selected from the group consisting of:
  a) hydrogen;
  b) hydroxy;

c) activated hydroxy;
d) azido;
e) $NH_2$;
f) cyano;
g) protected hydroxy;
h) protected amino;
i) -A-$R_4$, where A is O, S, S(O), $SO_2$, NH, $NCH_3$, NH(CO), NH(CO)NH or $NHSO_2$; and $R_4$ is independently selected from the group consisting of:
  (i) hydrogen;
  (ii) aryl; substituted aryl; heteroaryl; substituted heteroaryl;
  (iii) —$C_1$-$C_6$ alkyl, —$C_2$-$C_6$ alkenyl, or —$C_2$-$C_6$ alkynyl containing 0, 1, 2, or 3 heteroatoms selected from O, S or N, optionally substituted with one or more substituents selected from halogen, aryl, substituted aryl, heteroaryl, or substituted heteroaryl;
  (iv) —$C_3$-$C_{12}$ cycloalkyl containing 0, 1, 2, or 3 heteroatoms selected from O, S or N, optionally substituted with one or more substituents selected from halogen, aryl, substituted aryl, heteroaryl, or substituted heteroaryl;
  provided that when A=S(O) or $SO_2$, $R_4$ cannot be hydrogen;

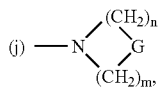

wherein G is absent, O, S, S(O), $S(O)_2$, $NR_4$, $N(CO)R_4$, $NSO_2R_4$, or $CHR_4$; n=1, 2, or 3; and m=2 or 3, where $R_3$ is as previously defined;

alternatively, $R_1$ and $R_2$ taken together with the carbon atom to which they are attached is selected from the group consisting of:
  a) C=O;
  b) C($OR_5$)($OR_6$), where $R_5$ and $R_6$ are selected from the group consisting of C1-C12 alkyl, aryl or substituted aryl; or taken together are —$(CH_2)_m$—, and where m is 2 or 3;
  c) C($SR_5$)($SR_6$), where $R_5$ and $R_6$ are as previously defined above;
  d) C=$CHR_4$, where $R_4$ is as previously defined;
  e) C=CNH (amino protecting group)
  f) C=N-Z-$R_4$, where Z is absent, O, NH, NH(CO), NH(CO)NH or $NHSO_2$; and $R_3$ is as previously defined;

X and Y are:
  (a) when one of X and Y is a hydrogen, the other is selected from:
    (i) hydrogen;
    (ii) deuterium;
    (iii) hydroxy;
    (iv) protected hydroxy;
    (v) amino;
    (vi) protected amino; and

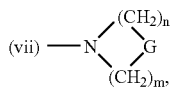

wherein G is absent, O, S, S(O), $S(O)_2$, $NR_4$, $N(CO)R_4$, $NSO_2R_4$, or $CHR_4$; n=1, 2, or 3; and m=2 or 3, where $R_4$ is as previously defined;
  b) X, Y taken together with the carbon atom to which they are attached is:
    (i) C=O;
    (ii) C=N—$OR_7$, wherein $R_7$ is selected from the group consisting of:
      1. hydrogen;
      2. —$CH_2O(CH_2)_2OCH_3$;
      3. —$CH_2O(CH_2O)_nCH_3$, wherein n is as previously defined;
      4. —$C_1$-$C_{12}$ alkyl, containing 0, 1, 2, or 3 heteroatoms, optionally substituted with one or more substituents selected from the group consisting of halogen, aryl, substituted aryl, heteroaryl and substituted heteroaryl;
      5. $C_3$-$C_{12}$ cycloalkyl;
      6. C(O)—$C_1$-$C_{12}$ alkyl;
      7. C(O)—($C_3$-$C_{12}$ cycloalkyl);
      8. C(O)—$R_4$, wherein $R_4$ is as previously defined; and
      9. —Si($R_a$)($R_b$)($R_c$), wherein $R_a$, $R_b$ and $R_c$ are each independently selected from the group consisting of $C_1$-$C_{12}$ alkyl, aryl and substituted aryl;
    (iii) C=N—O—C($R_8$)($R_9$)—O—$R_{10}$, wherein $R_8$ and $R_9$ taken together with the carbon atom to which they are attached form a $C_3$ to $C_{12}$ cycloalkyl group or each independently is selected from the group consisting of: hydrogen and $C_1$-$C_{12}$ alkyl; and $R_{10}$ is selected from the group consisting of:
      1. —$C_1$-$C_{12}$ alkyl, optionally substituted with one or more substituents selected from the group consisting of halogen, aryl, substituted aryl, heteroaryl and substituted heteroaryl;
      2. —$C_3$-$C_{12}$ cycloalkyl; and
      3. —Si($R_a$)($R_b$)($R_c$), wherein $R_a$, $R_b$ and $R_c$ are as previously defined;

Q is selected from the group consisting of:
  (a) hydrogen;
  (b) protected hydroxy;
  (c) $OR_{11}$, where $R_{11}$ is a group consisting of:
    (i) hydrogen;
    (ii) aryl; substituted aryl; heteroaryl; substituted heteroaryl;
    (iii) —$C_1$-$C_6$ alkyl, —$C_2$-$C_6$ alkenyl, or —$C_2$-$C_6$ alkynyl containing 0, 1, 2, or 3 heteroatoms selected from O, S or N, optionally substituted with one or more substituents selected from halogen, aryl, substituted aryl, heteroaryl, or substituted heteroaryl;
    (iv) —$C_3$-$C_{12}$ cycloalkyl or —$C_3$-$C_{12}$ substituted cycloalkyl containing 0, 1, 2, or 3 heteroatoms selected from O, S or N, optionally substituted with one or more substituents selected from halogen, aryl, substituted aryl, heteroaryl, or substituted heteroaryl;

B is $NR_{30}R_{40}$; wherein $R_{30}$ and $R_{40}$ is independently selected from the group consisting of hydrogen, acyl, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, saturated or unsaturated heterocyclic group; or can be taken together with the nitrogen atom to which they are attached to form a substituted or unsubstituted heterocyclic or heteroaromatic ring; preferably B is $N(CH_3)_2$;

V is selected from the group consisting of hydrogen, azido, cyano, nitro, aldehyde, carboxylic acid, amide, a substituted or unsubstituted, saturated or unsaturated aliphatic group; preferably V is $CH_3$;

L is selected from the group consisting of:
 (a) —$CH_2CH_3$;
 (b) —$CH(OH)CH_3$;
 (c) —$C_1$-$C_6$ alkyl, —$C_2$-$C_6$ alkenyl, or —$C_2$-$C_6$ alkynyl optionally substituted with one or more substituents selected from the group consisting of aryl, substituted aryl, heteroaryl, and substituted heteroaryl;

$R_x$ is hydrogen, hydroxylprotecting group or hydroxylprodrug group.

In another embodiment of the present invention there are disclosed pharmaceutical compositions comprising a therapeutically effective amount of a compound of the invention in combination with a pharmaceutically acceptable carrier or excipient. In yet another embodiment of the invention are methods of treating antibacterial infections in a subject in need of such treatment with said pharmaceutical compositions. Suitable carriers and formulations of the compounds of the present invention are disclosed.

DETAILED DESCRIPTION OF THE INVENTION

In a first embodiment of the compounds of the present invention are compounds represented by formula I as illustrated above, or a pharmaceutically acceptable salt, ester or prodrug thereof.

In a second embodiment of the compounds of the present invention are compounds represented by formula II as illustrated below, or a pharmaceutically acceptable salt, ester or prodrug thereof:

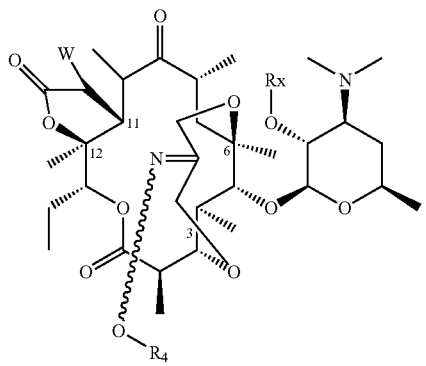

(II)

where W, $R_4$ and $R_x$ are as previously defined.

In a third embodiment of the compounds of the present invention are compounds represented by formula III as illustrated below, or a pharmaceutically acceptable salt, ester or prodrug thereof:

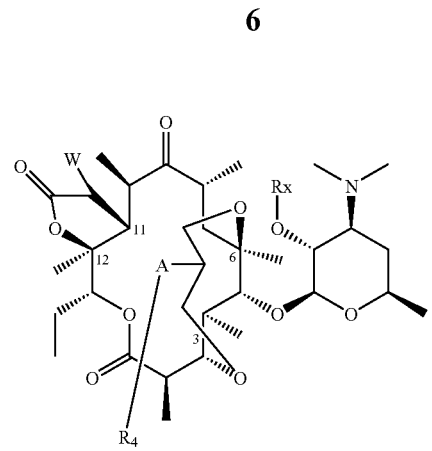

(III)

where W, $R_4$ and $R_x$ are as previously defined.

In a fourth embodiment of the compounds of the present invention are compounds represented by formula IV as illustrated below, or a pharmaceutically acceptable salt, ester or prodrug thereof:

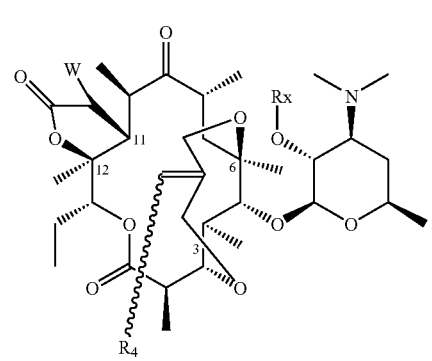

(IV)

where W, $R_4$ and $R_x$ are as previously defined.

In a fifth embodiment of the compounds of the present invention are compounds represented by formula V as illustrated below, or a pharmaceutically acceptable salt, ester or prodrug thereof:

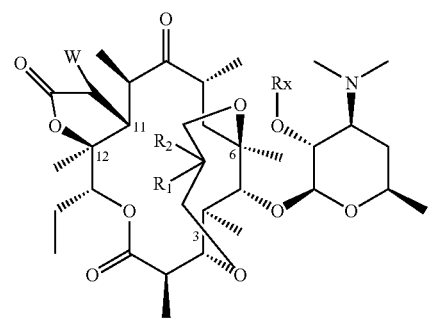

(V)

where W, $R_1$, $R_2$ and $R_x$ are as previously defined.

Representative compounds according to the invention are those selected from the group consisting of:

(1) Compound of formula V, wherein $R_1$ and $R_2$ taken together with the carbon atom to which they are attached are $C=CH_2$, $W=[—S(CH_2)_2Ph]$ and $Rx=Ac$;
(2) Compound of formula V, wherein $R_1$ and $R_2$ taken together with the carbon atom to which they are attached are $C=CH_2$, $W=[—S(CH_2)_2Ph]$ and $Rx=H$;
(3) Compound of formula V, wherein $R_1$ and $R_2$ taken together with the carbon atom to which they are attached are $C=CH_2$, $W=CO_2Me$, and $Rx=Ac$.
(4) Compound of formula V, wherein $R_1$ and $R_2$ taken together with the carbon atom to which they are attached are $C=CH_2$, $W=H$ and $Rx=Ac$.
(5) Compound of formula V, wherein $R_1$ and $R_2$ taken together with the carbon atom to which they are attached are $C=CH_2$, and $W=Rx=H$.
(6) Compound of formula V, wherein $R_1$ and $R_2$ taken together with the carbon atom to which they are attached are $C=O$, and $W=Rx=H$.
(7) Compound of formula V, wherein $R_1$ and $R_2$ taken together with the carbon atom to which they are attached are $C=NO[6'\text{-amino-}[2,2']\text{bipyridinyl-6-ylmethyl}]$, $W=Rx=H$.

Further representative species of the present invention are:
Compounds (8)-(115) of the formula (A):

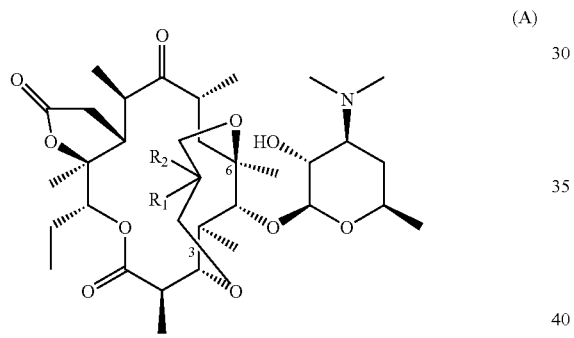

(A)

wherein $R_1$ and $R_2$ taken together with the carbon to which they are attached $(CR_1R_2)$, $R_{20}$ and $Rx$ are delineated for each example in Table 1.

TABLE 1

| Compound | $CR_1R_2$ |
|---|---|
| (8) | C=N—O—CH₂—C≡CH |
| (9) | C=N—O—CH₂—(2-(thiazol-2-yl)phenyl) |
| (10) | C=N—O—CH₂—(3-(thiazol-2-yl)phenyl) |
| (11) | C=N—O—CH₂—(4-(thiazol-2-yl)phenyl) |
| (12) | C=N—O—CH₂—(benzotriazol-1-yl) |
| (13) | C=N—O—CH₂—(1-methyl-1H-benzotriazol-5-yl) |
| (14) | C=N—O—CH₂—(4-biphenyl) |
| (15) | C=N—O—CH₂—(2-naphthyl) |
| (16) | C=N—O—CH₂—(quinolin-2-yl) |
| (17) | C=N—O—CH₂—(1-naphthyl) |
| (18) | C=N—O—CH₂—(2-biphenyl) |
| (19) | C=N—O—CH₂—(3-biphenyl) |

TABLE 1-continued
| Compound | CR₁R₂ |
|---|---|
| (20) |  |
| (21) |  |
| (22) |  |
| (23) |  |
| (24) |  |
| (25) |  |
| (26) |  |
| (27) |  |
| (28) |  |
| (29) |  |
| (30) | 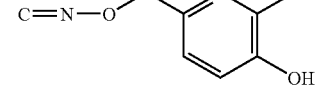 |
| (31) | 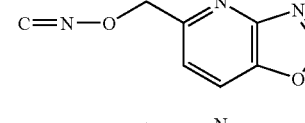 |
| (32) | 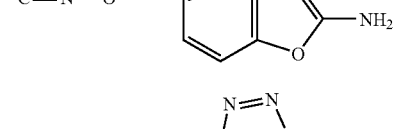 |
| (33) | 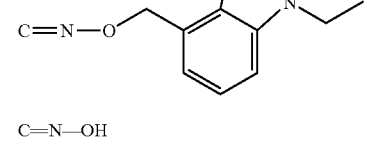 |
| (34) | C=N—OH |
| (35) | 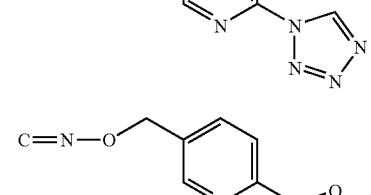 |
| (36) | 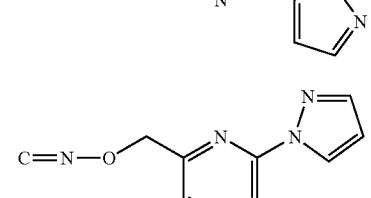 |
| (37) | 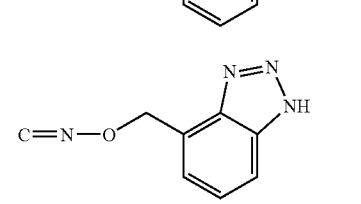 |
| (38) | 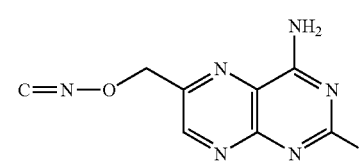 |
| (39) | 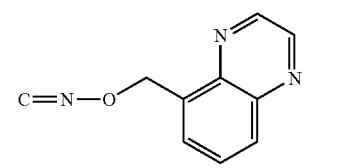 |
| (40) |  |

TABLE 1-continued

| Compound | CR₁R₂ |
|---|---|
| (41) | pyrido-pyrazine-CH₂-O-N=C |
| (42) | quinoline-CH₂-O-N=C |
| (43) | pyrido-pyrazine-CH₂-O-N=C |
| (44) | triazolopyridine-CH₂-O-N=C |
| (45) | triazolopyridine-CH₂-O-N=C |
| (46) | (2,2'-bipyridine)-CH₂-O-N=C |
| (47) | (6-fluoro-2,2'-bipyridine)-CH₂-O-N=C |
| (48) | (pyridine-pyrimidine)-CH₂-O-N=C |
| (49) | (2-chloro-bipyridine)-CH₂-O-N=C |
| (50) | (2-fluoro-bipyridine)-CH₂-O-N=C |
| (51) | (pyridine-pyrazine)-CH₂-O-N=C |
| (52) | (bipyridine)-CH₂-O-N=C |
| (53) | (5-bromo-pyridine-pyrimidine)-CH₂-O-N=C |
| (54) | (pyridine-pyrimidine)-CH₂-O-N=C |
| (55) | (6-amino-bipyridine)-CH₂-O-N=C |
| (56) | (6-hydroxy-bipyridine)-CH₂-O-N=C |
| (57) | (6-amino-pyridine-pyrazine)-CH₂-O-N=C |
| (58) | (6-cyano-pyridine)-CH₂-O-N=C |

TABLE 1-continued
| Compound | CR₁R₂ |
|---|---|
| (59) | 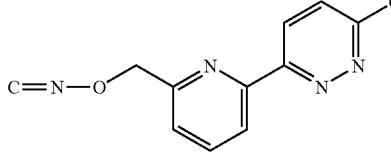 |
| (60) | 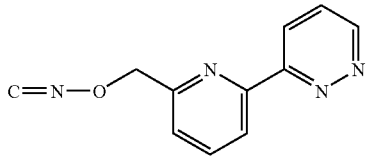 |
| (61) | 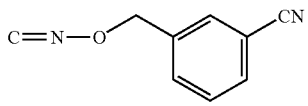 |
| (62) | 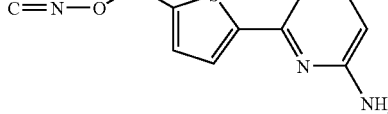 |
| (63) | 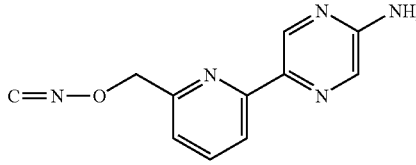 |
| (64) | 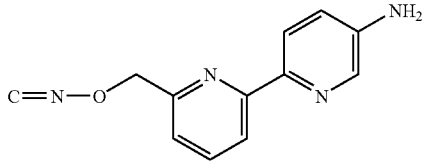 |
| (65) | 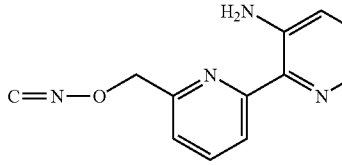 |
| (66) | 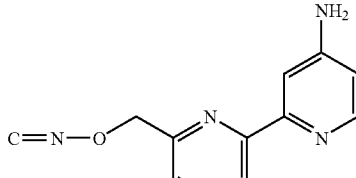 |
| (67) | 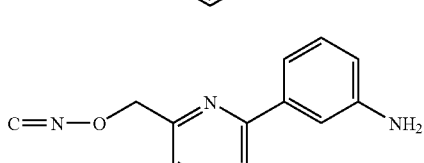 |
| (68) | 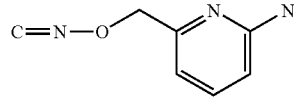 |
| (69) | 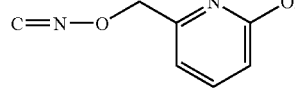 |
| (70) | 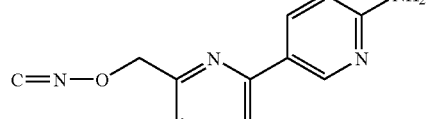 |
| (71) | 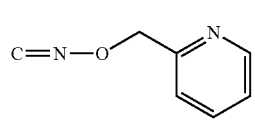 |
| (72) | 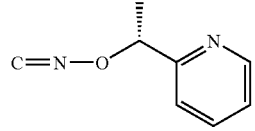 |
| (73) | 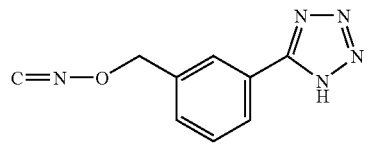 |
| (74) | 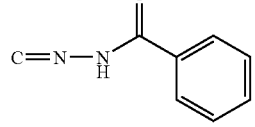 |
| (75) | 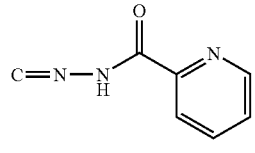 |
| (76) | 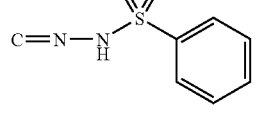 |
| (77) | 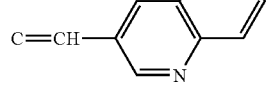 |
| (78) | 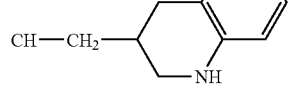 |

TABLE 1-continued
| Compound | CR₁R₂ |
|---|---|
| (79) | 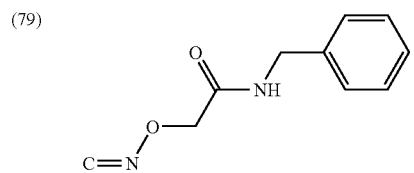 |
| (80) | 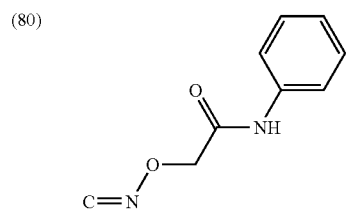 |
| (81) | 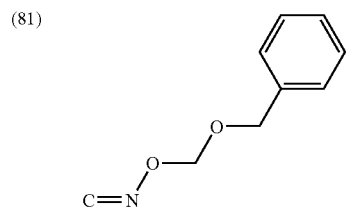 |
| (82) | 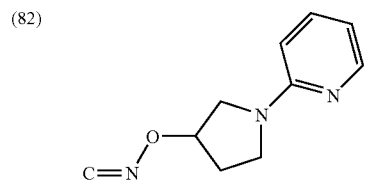 |
| (83) | 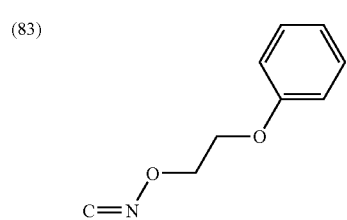 |
| (84) | 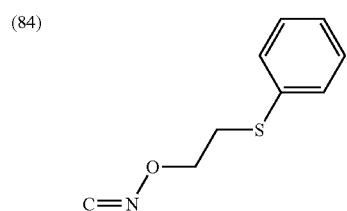 |
| (85) | 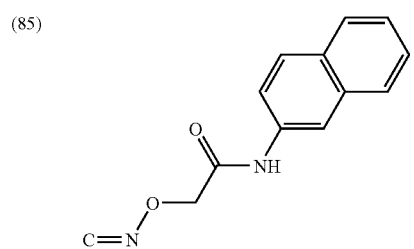 |
| (86) | 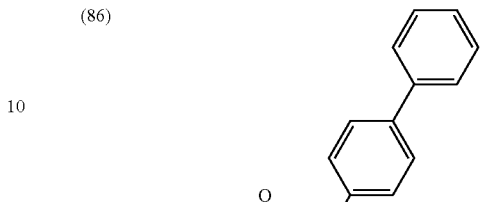 |
| (87) | 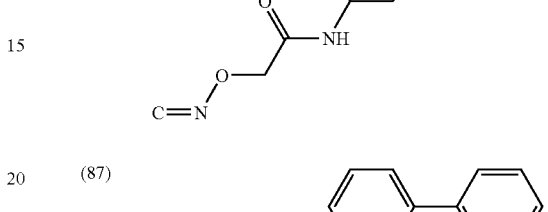 |
| (88) | 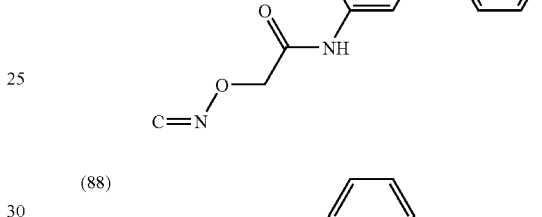 |
| (89) | 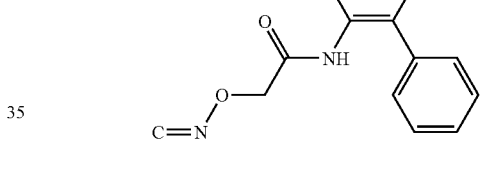 |
| (90) | 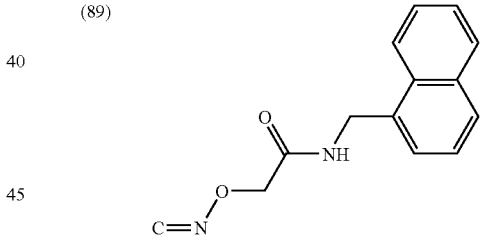 |
| (91) | 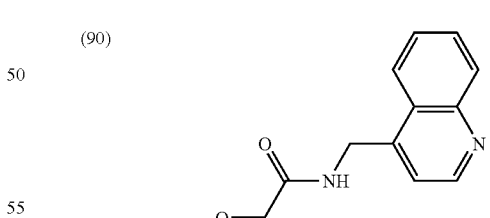 |

TABLE 1-continued
| Compound | CR₁R₂ |
|---|---|
| (92) | 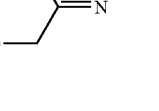 |
| (93) | 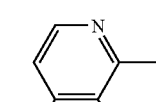 |
| (94) | 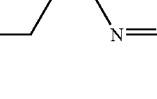 |
| (95) | 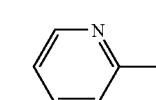 |
| (96) | 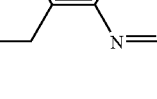 |
| (97) | 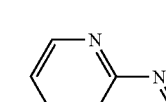 |
| (98) | 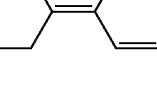 |
| (99) | 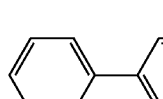 |
| (100) | 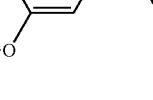 |
| (101) | 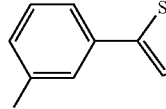 |
| (102) |  |
| (103) |  |
| (104) |  |
| (105) |  |
| (106) |  |
| (107) |  |

TABLE 1-continued

| Compound | CR₁R₂ |
|---|---|
| (108) |  |
| (109) | 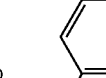 |
| (110) | 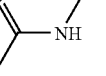 |
| (111) | 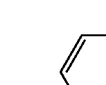 |
| (112) | 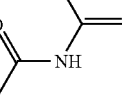 |
| (113) |  |
| (114) | 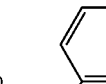 |
| (115) | 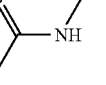 |

Further representative species of the present invention are:

Compounds (116)-(179) of the formula (A):

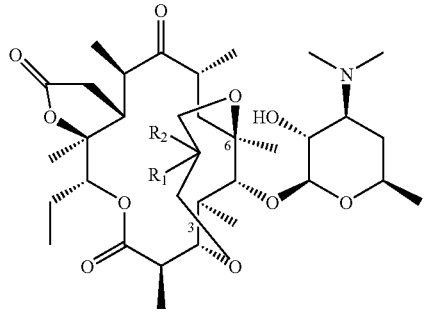

(A)

wherein $R_1$, and $R_2$ are delineated for each example in Table 2.

TABLE 2

| Compound | R₁ | R₂ |
|---|---|---|
| (116) | phenylethyl (H₂C–CH₂–C₆H₅) | OH |
| (117) | phenoxy (O–C₆H₅) | H |
| (118) | quinolin-4-yloxy | H |
| (119) | benzylamino (HN–CH₂–C₆H₅) | H |
| (120) | N-methyl-N-benzylamino | H |
| (121) | phenethylamino (HN–CH₂CH₂–C₆H₅) | H |
| (122) | 3-phenylpropylamino | H |

TABLE 2-continued

| Compound | R₁ | R₂ |
|---|---|---|
| (123) | 1-naphthyl-CH₂CH₂-NH- | H |
| (124) | 2-naphthyl-CH₂CH₂-NH- | H |
| (125) | 2-naphthyl-CH₂CH₂-N(CH₃)- | H |
| (126) | 3-quinolinyl-CH=CH-CH₂-O- | H |
| (127) | 4-quinolinyl-CH=CH-CH₂-O- | H |
| (128) | phenyl-NH-C(O)-O- | H |
| (129) | benzyl-NH-C(O)-O- | H |
| (130) | N₃ | H |
| (131) | NH₂ | H |
| (132) | benzyl-O-C(O)-NH- | H |
| (133) | phenyl-C(O)-NH- | H |
| (134) | benzyl-C(O)-NH- | H |
| (135) | benzyl-NH-C(O)-NH- | H |
| (136) | phenyl-NH-C(O)-NH- | H |
| (137) | benzyl-S(O)₂-NH- | H |
| (138) | phenyl-S(O)₂-NH- | H |
| (139) | 2-pyridinyl-S(O)₂-NH- | H |
| (140) | 3-pyridinyl-S(O)₂-NH- | H |
| (141) | 3-biphenyl-S(O)₂-NH- | H |

TABLE 2-continued

| Compound | R₁ | R₂ |
|---|---|---|
| (142) | quinoline-8-sulfonamide | H |
| (143) | biphenyl-4-sulfonamide | H |
| (144) | 5-(isoxazol-5-yl)thiophene-2-sulfonamide | H |
| (145) | naphthalene-1-sulfonamide | H |
| (146) | naphthalene-2-sulfonamide | H |
| (147) | thiophene-2-sulfonamide | H |
| (148) | 5-(isoxazol-3-yl)thiophene-2-sulfonamide | H |
| (149) | (E)-2-phenylethenesulfonamide | H |
| (150) | benzofuran-2-sulfonamide | H |
| (151) | benzothiazole-6-sulfonamide | H |
| (152) | 4-(pyrazol-1-yl)benzenesulfonamide | H |
| (153) | 6-phenoxypyridine-3-sulfonamide | H |
| (154) | benzothiophene-2-sulfonamide | H |
| (155) | 3-(pyridin-3-yl)benzenesulfonamide | H |
| (156) | 3-(pyrazin-2-yl)benzenesulfonamide | H |
| (157) | 3-(pyridin-2-yl)benzenesulfonamide | H |

TABLE 2-continued

| Compound | R₁ | R₂ |
|---|---|---|
| (158) | 3-(6-aminopyridin-2-yl)benzenesulfonamide | H |
| (159) | 3,4-dichlorobenzenesulfonamide | H |
| (160) | 3,4-difluorobenzenesulfonamide | H |
| (161) | 3-fluorobenzenesulfonamide | H |
| (162) | 4-fluorobenzenesulfonamide | H |
| (163) | 3-methoxybenzenesulfonamide | H |
| (164) | 4-methoxybenzenesulfonamide | H |
| (165) | 3-chlorobenzenesulfonamide | H |
| (166) | N-methylbenzo[b]thiophene-2-sulfonamide | H |
| (167) | (6-(1H-pyrazol-1-yl)pyridin-3-yl)methyl carbamate | H |
| (168) | (6-(1H-pyrazol-1-yl)pyridin-2-yl)methyl carbamate | H |
| (169) | quinolin-3-ylmethyl carbamate | H |
| (170) | quinolin-4-ylmethyl carbamate | H |
| (171) | quinoline-4-carboxamide | H |
| (172) | quinoline-3-carboxamide | H |

TABLE 2-continued

| Compound | R₁ | R₂ |
|---|---|---|
| (173) | (isoquinolin-3-ylacetamide group) | H |
| (174) | (naphthalen-1-ylacetamide group) | H |
| (175) | (6-(1H-pyrazol-1-yl)pyridin-3-yl acetamide group) | H |
| (176) | (6-(1H-pyrazol-1-yl)pyridin-2-yl acetamide group) | H |
| (177) | (N-phenyl propanamide group) | H |
| (178) | (N-(naphthalen-1-yl) propanamide group) | H |
| (179) | (N-(naphthalen-2-yl) propanamide group) | H |

Further representative species of the present invention are:
Compounds (180)-(341) of the formula B:

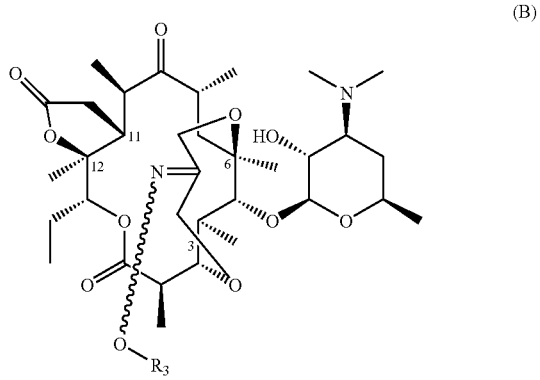

wherein $R_3$ is delineated for each example in Table 3.

TABLE 3

| Compound | R₃ |
|---|---|
| (180) | 4-nitrobenzyl |
| (181) | 4-phenylbut-3-yn-1-yl |
| (182) | 2-(pyridin-3-yl)ethyl |
| (183) | 2-(5-(pyridin-2-yl)thiophen-2-yl)ethyl |
| (184) | quinolin-3-ylmethyl |
| (185) | (E)-4-phenylbut-3-en-1-yl |

TABLE 3-continued
| Compound | R₃ |
|---|---|
| (186) | 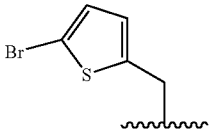 |
| (187) | 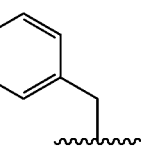 |
| (188) | 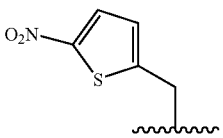 |
| (189) | 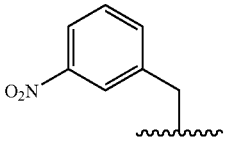 |
| (190) | 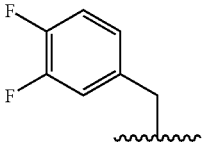 |
| (191) | 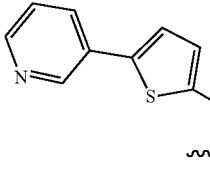 |
| (192) | 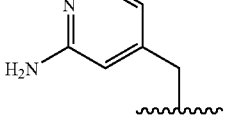 |
| (193) | 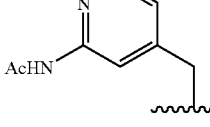 |
| (194) | 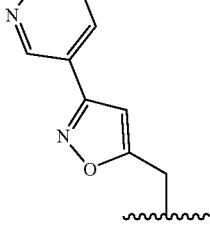 |
| (195) | 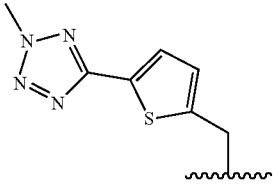 |
| (196) | 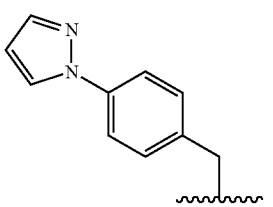 |
| (197) | 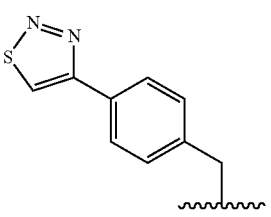 |
| (198) | 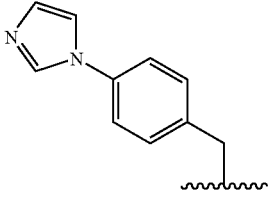 |
| (199) | 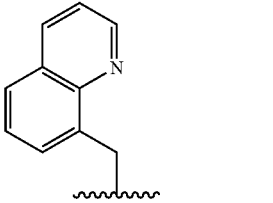 |
| (200) | 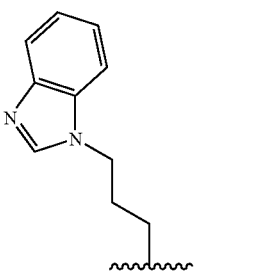 |

TABLE 3-continued
| Compound | R₃ |
|---|---|
| (201) | 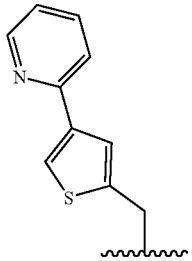 |
| (202) | 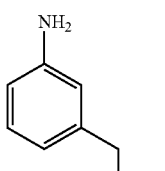 |
| (203) | 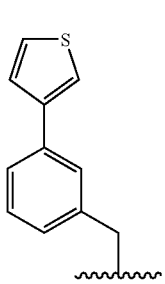 |
| (204) | 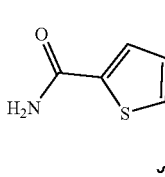 |
| (205) | 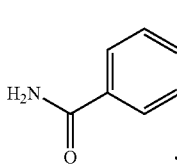 |
| (206) | 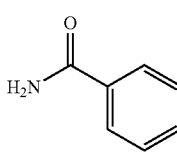 |
| (207) | 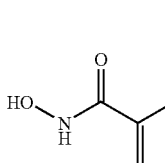 |
| (208) | 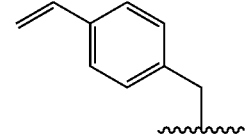 |
| (209) | 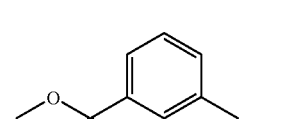 |
| (210) | 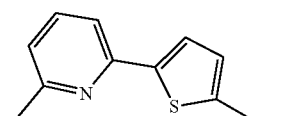 |
| (211) | 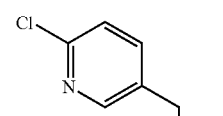 |
| (212) | 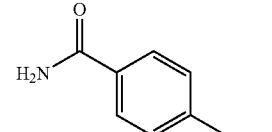 |
| (213) | 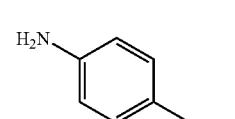 |
| (214) | 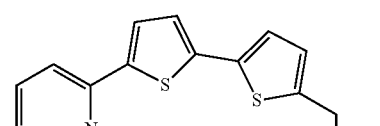 |
| (215) | 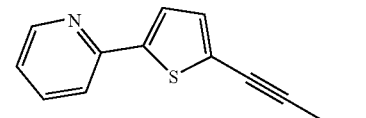 |

TABLE 3-continued
| Compound | R₃ |
|---|---|
| (216) | 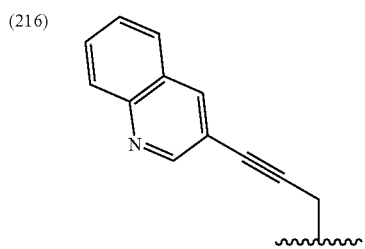 |
| (217) | 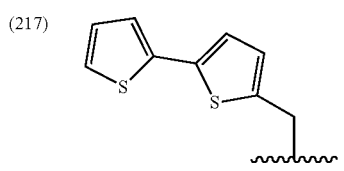 |
| (218) | 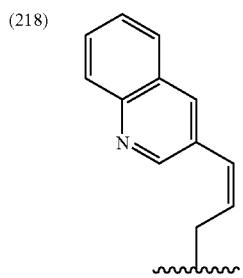 |
| (219) | 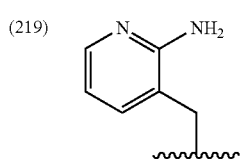 |
| (220) | 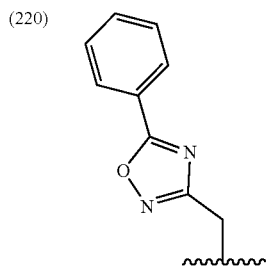 |
| (221) | 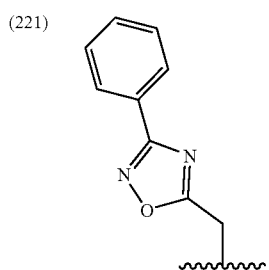 |
| (222) | |
| (223) | |
| (224) | |
| (225) | |
| (226) | |
| (227) | |
| (228) | |

TABLE 3-continued
| Compound | R3 |
|---|---|
| (229) | 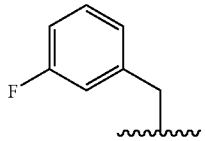 |
| (230) | 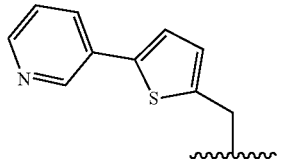 |
| (231) | 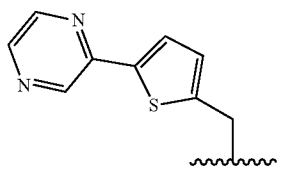 |
| (232) | 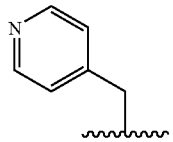 |
| (233) | 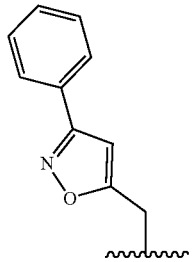 |
| (234) | 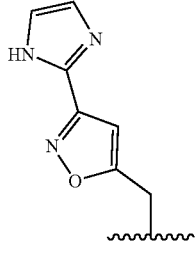 |
| (235) | 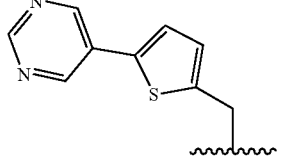 |
| (236) | 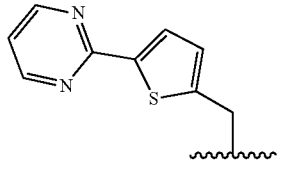 |
| (237) | 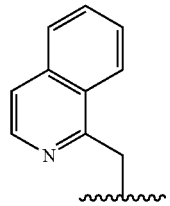 |
| (238) | 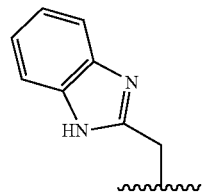 |
| (239) | 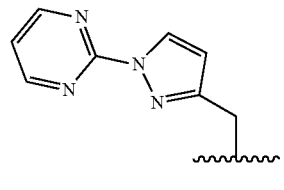 |
| (240) | 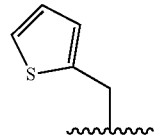 |
| (241) | 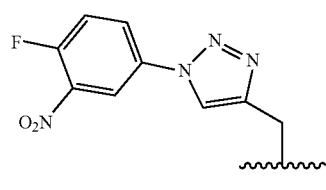 |
| (242) | 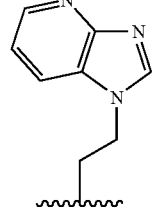 |
| (243) | 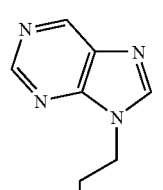 |
| (244) | 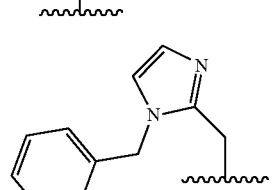 |

TABLE 3-continued

| Compound | R₃ |
|---|---|
| (245) | [structure] |
| (246) | [structure] |
| (247) | [structure] |
| (248) | [structure] |
| (249) | [structure] |
| (250) | [structure] |
| (251) | [structure] |
| (252) | [structure] |
| (253) | [structure] |
| (254) | [structure] |
| (255) | [structure] |
| (256) | [structure] |
| (257) | [structure] |
| (258) | [structure] |
| (259) | [structure] |
| (260) | [structure] |

TABLE 3-continued

| Compound | R₃ |
|---|---|
| (261) | *N-methyl 4-substituted benzamide* |
| (262) | *N-ethyl 4-substituted benzamide* |
| (263) | *methyl 4-substituted benzoate* |
| (264) | *N-cyclopropyl 4-substituted benzamide* |
| (265) | *benzyl oxime of 5-substituted thiophene-2-carbaldehyde* |
| (266) | *phenyl oxime of 5-ethyl thiophene-2-carbaldehyde* |
| (267) | *methyl oxime of 5-substituted thiophene-2-carbaldehyde* |
| (268) | *2-(3,4-dimethoxyphenyl)-5-substituted thiophene* |
| (269) | *methyl 3-methoxy-4-substituted benzoate* |
| (270) | *3-methoxy-4-substituted benzamide* |
| (271) | *4-acetamido substituted benzene* |
| (272) | *5-cyano-2-substituted thiophene* |
| (273) | *4-substituted benzohydrazide* |
| (274) | *methyl 4-substituted phenylcarbamate* |
| (275) | *N-hydroxy 4-substituted benzamide* |

TABLE 3-continued
| Compound | R₃ |
|---|---|
| (276) | 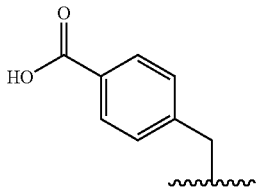 |
| (277) | 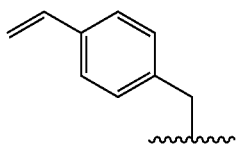 |
| (278) | 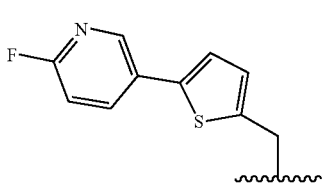 |
| (279) | 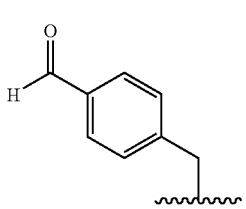 |
| (280) | 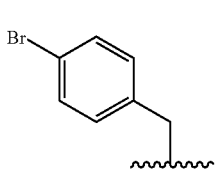 |
| (281) | 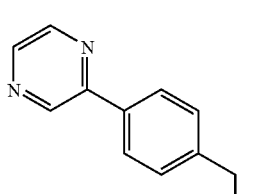 |
| (282) | 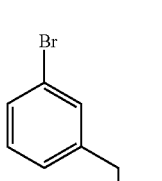 |
| (283) |  |
| (284) |  |
| (285) |  |
| (286) |  |
| (287) |  |

TABLE 3-continued
| Compound | R₃ |
|---|---|
| (288) | 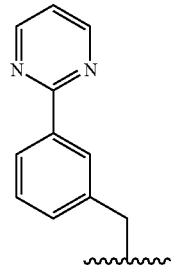 |
| (289) | 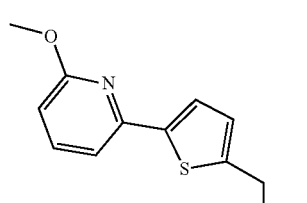 |
| (290) | 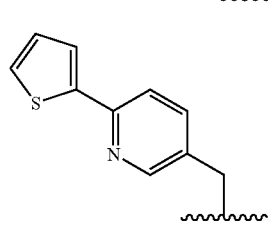 |
| (291) | 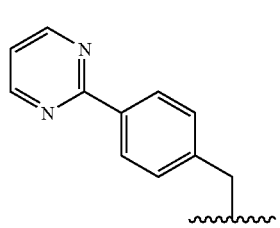 |
| (292) | 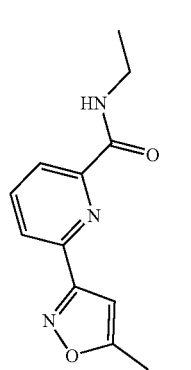 |
| (293) | 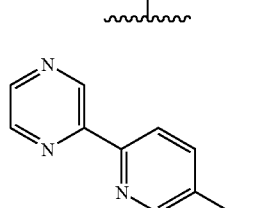 |
| (294) | |
| (295) | |
| (296) | |
| (297) | |
| (298) | |
| (299) | |
| (300) | |

TABLE 3-continued
| Compound | R₃ |
|---|---|
| (301)–(305) | 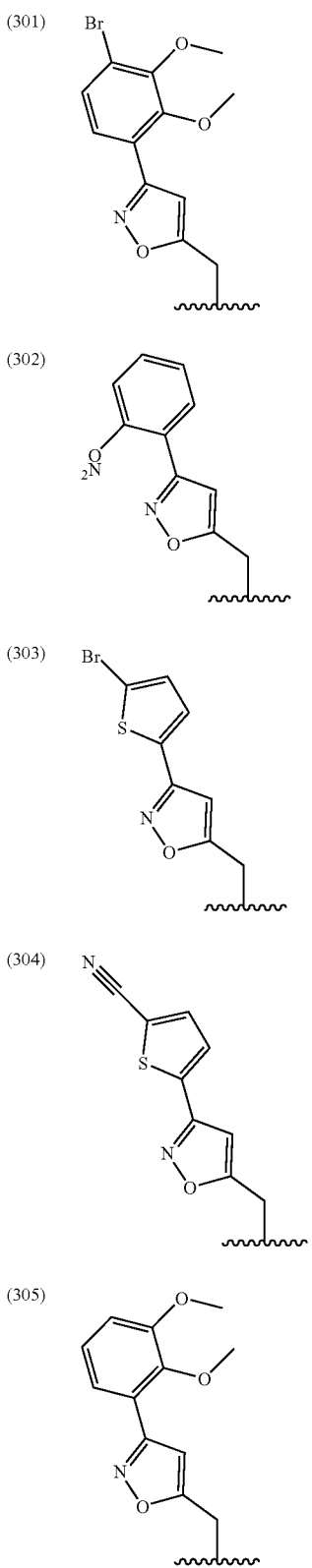 |
| (306)–(313) | 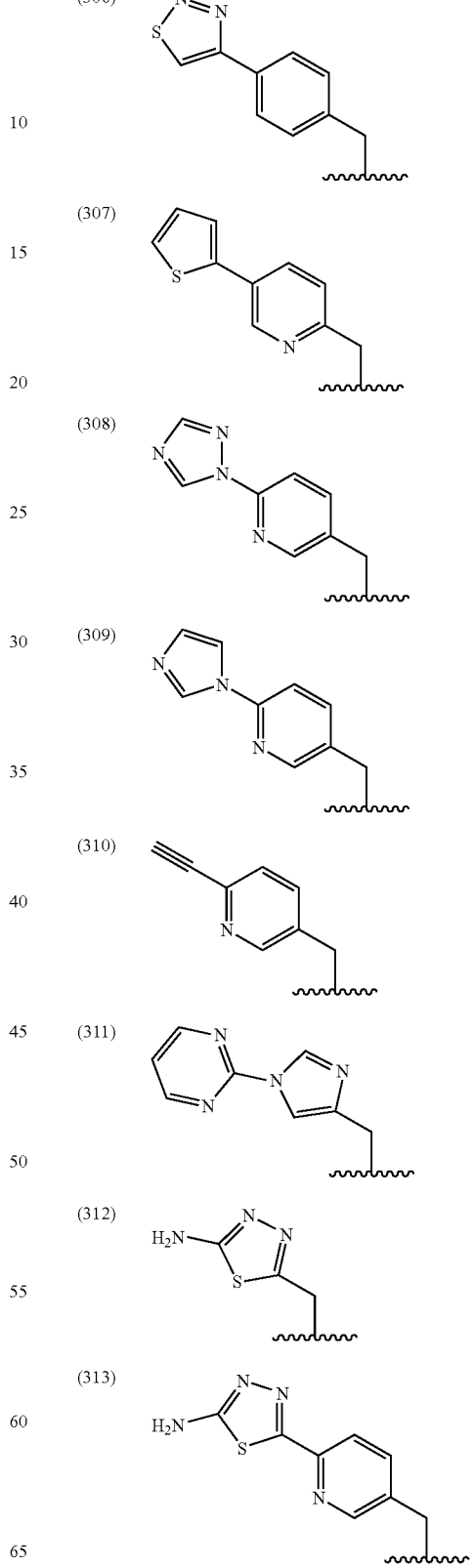 |

TABLE 3-continued
| Compound | R₃ |
|---|---|
| (314) | 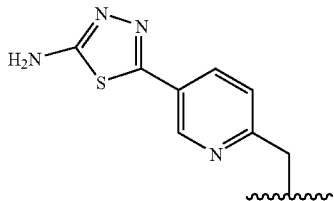 |
| (315) | 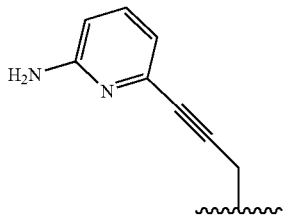 |
| (316) | 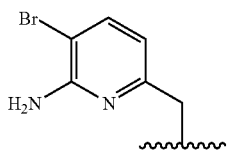 |
| (317) | 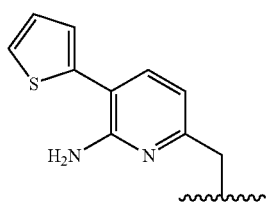 |
| (318) | 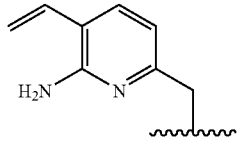 |
| (319) | 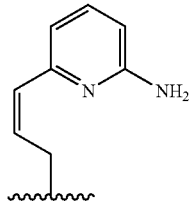 |
| (320) | 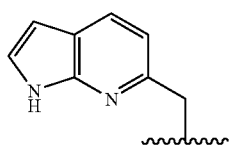 |
| (321) | 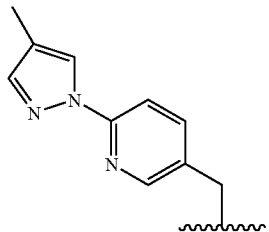 |
| (322) | 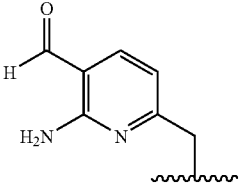 |
| (323) | 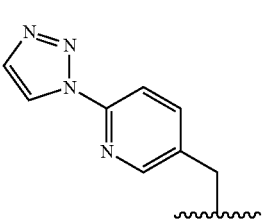 |
| (324) | 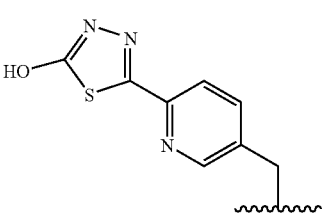 |
| (325) | 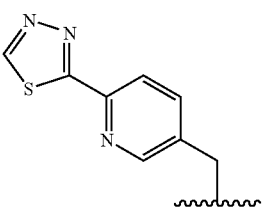 |
| (326) | 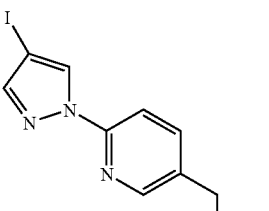 |
| (327) | 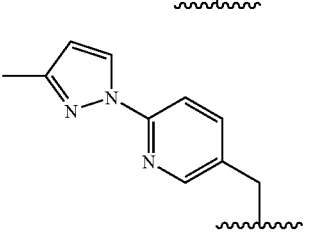 |
| (328) | 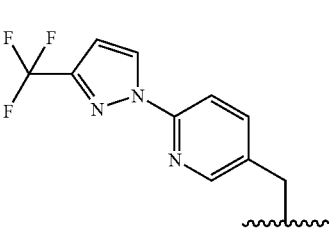 |

TABLE 3-continued
| Compound | R₃ |
|---|---|
| (329) | 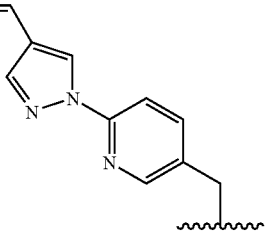 |
| (330) | 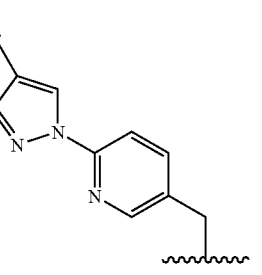 |
| (331) | 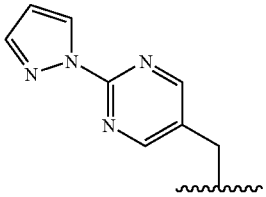 |
| (332) | 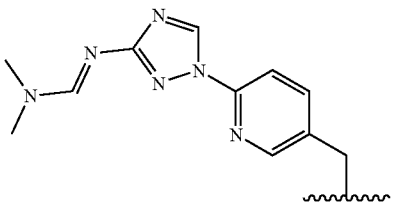 |
| (333) | 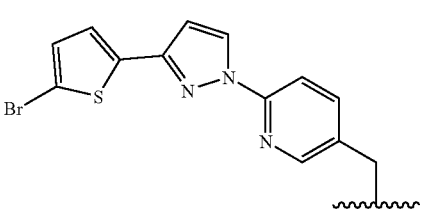 |
| (334) | 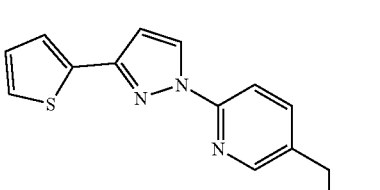 |
| (335) | 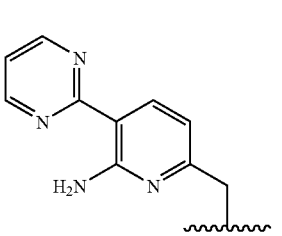 |
TABLE 3-continued
| Compound | R₃ |
|---|---|
| (336) | 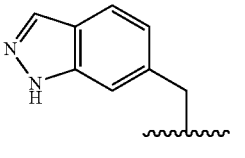 |
| (337) | 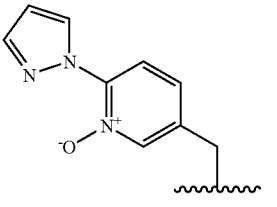 |
| (338) | 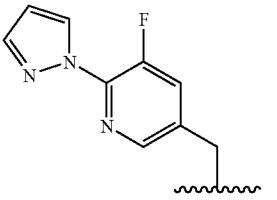 |
| (339) | 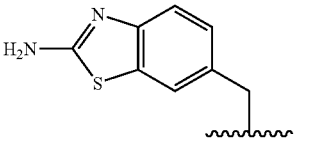 |
| (340) | 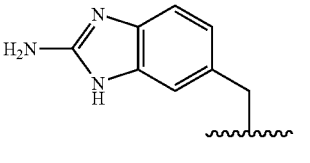 |
| (341) | 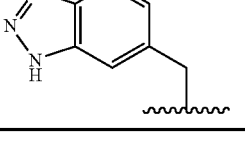 |
Further representative species of the present invention are:
Compounds (342)-(363) of the formula C:
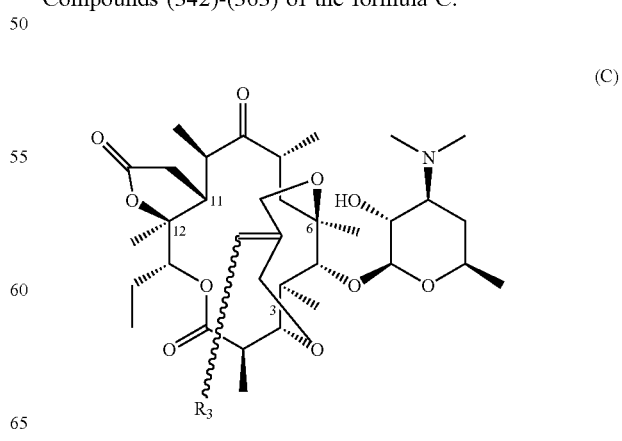
(C)
wherein R₃ is delineated for each example in Table 4.

TABLE 4
| Compound | R₃ |
|---|---|
| (342) | 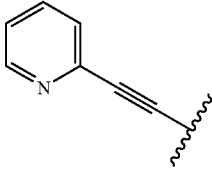 |
| (343) | 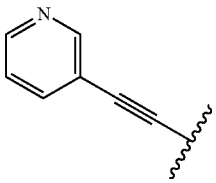 |
| (344) | 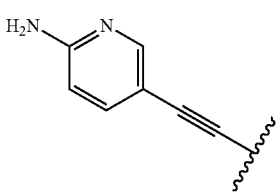 |
| (345) | 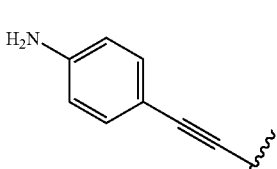 |
| (346) | 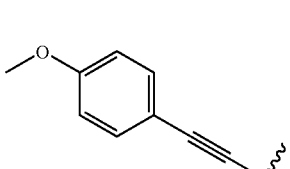 |
| (347) | 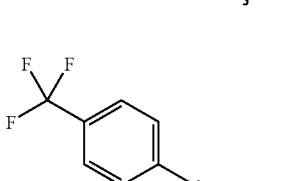 |
| (348) | 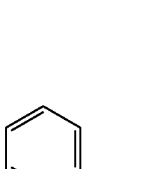 |
| (349) | 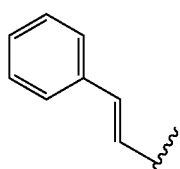 |
| (350) | 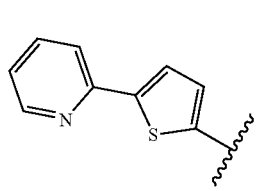 |
| (351) | 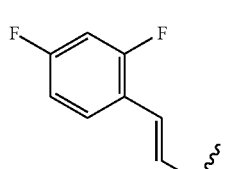 |
| (352) | 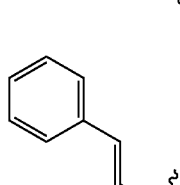 |
| (353) | 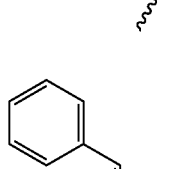 |
| (354) | 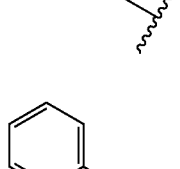 |
| (355) | 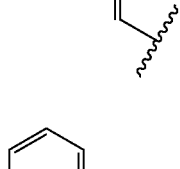 |

TABLE 4-continued

| Compound | R$_3$ |
|---|---|
| (356) | 1H-benzimidazol-2-yl |
| (357) | cinnamyl (3-phenylprop-2-en-1-yl) |
| (358) | cinnamyl |
| (359) | 3-(4-nitrophenyl)prop-2-en-1-yl |
| (360) | 3-(3-chloro-4-fluorophenyl)prop-2-en-1-yl |
| (361) | 3-(4-methoxyphenyl)prop-2-en-1-yl |
| (362) | 3-(3-chlorophenyl)prop-2-en-1-yl |

TABLE 4-continued

| Compound | R$_3$ |
|---|---|
| (363) | 1H-benzimidazol-2-yl |

Further representative species of the present invention are:
Compounds (364)-(405) of the formula D:

(D)

wherein W is delineated for each example in Table 5.

TABLE 5

| Compound | W |
|---|---|
| (364) | phenethylthio (PhCH$_2$CH$_2$S–) |
| (365) | CN |
| (366) | H |
| (367) | (4-methoxybenzyl)thio |
| (368) | (4-methoxybenzyl)sulfonyl |
| (369) | (6-nitropyridin-2-yl)disulfanyl |

TABLE 5-continued

| Compound | W |
|---|---|
| (370) | quinolin-8-yl-NH-C(=O)-CH2-S-⁀ |
| (371) | CH3O-C(=O)-CH2-S-⁀ |
| (372) | 2-oxo-1,2,3,4-tetrahydroquinolin-6-yl-C(=O)-CH2-S-⁀ |
| (373) | pyridin-2-yl-C(=O)-CH2-S-⁀ |
| (374) | 1,2,3,4-tetrahydroisoquinolin-2-yl-C(=O)-CH2CH2-S-⁀ |
| (375) | 6-amino-9H-purin-9-yl-CH2CH2-N(CH3)-CH2CH2-S-⁀ |
| (376) | 3-phenyl-1H-pyrazol-1-yl-CH2CH2CH2-S-⁀ |
| (377) | 3-phenyl-1H-pyrazol-1-yl-CH2CH2CH2-S(=O)2-⁀ |
| (378) | 3-(pyridin-3-yl)-1H-1,2,4-triazol-1-yl-CH2CH2-S-⁀ |
| (379) | 4-amino-1H-pyrazolo[3,4-d]pyrimidin-1-yl-CH2CH2CH2-S-⁀ |
| (380) | (5-methyl-2,4-dioxo-3,4-dihydropyrimidin-1(2H)-yl)-CH2-O-CH2CH2-S-⁀ |
| (381) | PhCH2-O-C(=O)-⁀ |
| (382) | 4-(dimethylamino)phenyl-C(=O)-CH2-S-⁀ |
| (383) | indolin-1-yl-C(=O)-CH2-S-⁀ |
| (384) | pyridin-3-yl-C(=O)-NH-CH2CH2-S-⁀ |
| (385) | benzo[c][1,2,5]oxadiazol-5-yl-C(=O)-NH-CH2CH2-S-⁀ |
| (386) | benzo[c][1,2,5]oxadiazol-4-yl-S(=O)2-NH-CH2CH2-S-⁀ |

TABLE 5-continued

| Compound | W |
|---|---|
| (387) | [structure: 5-(pyridin-2-yl)thiophene-2-sulfonamide-NH-CH2CH2-S-] |
| (388) | [structure: 4-cyanophenyl-C≡C-CH2-S-] |
| (389) | [structure: benzyl-NH-SO2-CH2CH2-S-] |
| (390) | [structure: quinolin-5-yl-NH-C(O)-CH2-S-] |
| (391) | [structure: quinoline-3-carboxamide-NH-CH2CH2-S-] |
| (392) | [structure: quinolin-8-yl-SO2-NH-CH2CH2-S-] |
| (393) | [structure: benzo[1,3]dioxol-5-yl-CH2-NH-C(O)-CH2-S-] |
| (394) | [structure: furan-2-yl-CH2-NH-C(O)-CH2-S-] |
| (395) | [structure: pyridin-2-yl-CH2-NH-C(O)-CH2-S-] |
| (396) | [structure: 5-methylisoxazol-3-yl-NH-C(O)-CH2-S-] |
| (397) | [structure: benzothiazol-2-yl-CH2-NH-C(O)-CH2-S-] |
| (398) | [structure: imidazol-2-yl-CH2-NH-C(O)-CH2-S-] |
| (399) | [structure: 6-(pyrazol-1-yl)pyridin-3-yl-NH-C(O)-CH2-S-] |
| (400) | [structure: benzo[b]thiophen-3-yl-NH-C(O)-CH2-S-] |
| (401) | [structure: 9H-purin-6-yl-NH-CH2CH2-S-] |
| (402) | [structure: pyridin-2-yl-CH2CH2-NH-C(O)-] |
| (403) | [structure: pyridin-3-yl-CH2CH2-NH-C(O)-] |
| (404) | [structure: quinoxalin-2-yl-S-CH2-C(O)-NH-] |
| (405) | [structure: 4-(pyridin-3-yl)imidazol-1-yl-CH2CH2-NH-] |

A further embodiment of the present invention includes pharmaceutical compositions comprising any single compound delineated herein, or a pharmaceutically acceptable salt, ester, or prodrug thereof, with a pharmaceutically acceptable carrier or excipient.

Yet another embodiment of the present invention is a pharmaceutical composition comprising a combination of two or more compounds delineated herein, or a pharmaceutically acceptable salt, ester, or prodrug thereof, with a pharmaceutically acceptable carrier or excipient.

Yet a further embodiment of the present invention is a pharmaceutical composition comprising any single compound delineated herein in combination with one or more antibiotics known in the art, or a pharmaceutically acceptable salt, ester, or prodrug thereof, with a pharmaceutically acceptable carrier or excipient.

In addition, the present invention contemplates processes of making any compound delineated herein via any synthetic method delineated herein.

DEFINITIONS

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system having one or two aromatic rings including, but not limited to, phenyl, naphthyl, tetrahydronaphthyl, indanyl, idenyl and the like.

The term "heteroaryl," as used herein, refers to a mono- or polycyclic (e.g. bi-, or tri-cyclic or more) aromatic radical or ring having from five to ten ring atoms of which one or more ring atom is selected from, for example, S, O and N; zero, one or two ring atoms are additional heteroatoms independently selected from, for example, S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

In accordance with the invention, any of the aryls, substituted aryls, heteroaryls and substituted heteroaryls described herein, can be any aromatic group. Aromatic groups can be substituted or unsubstituted.

The terms "$C_1$-$C_6$ alkyl," or "$C_1$-$C_{12}$ alkyl," as used herein, refer to saturated, straight- or branched-chain hydrocarbon radicals containing between one and six, or one and twelve carbon atoms, respectively. Examples of $C_1$-$C_6$ alkyl radicals include, but are not limited to, methyl, ethyl, propyl, isopropyl, n-butyl, tert-butyl, neopentyl and n-hexyl radicals; and examples of $C_1$-$C_{12}$ alkyl radicals include, but are not limited to, ethyl, propyl, isopropyl, n-hexyl, octyl, decyl, dodecyl radicals.

The term "$C_2$-$C_6$ alkenyl," as used herein, denotes a monovalent group derived from a hydrocarbon moiety containing from two to six carbon atoms having at least one carbon-carbon double bond by the removal of a single hydrogen atom. Alkenyl groups include, but are not limited to, for example, ethenyl, propenyl, butenyl, 1-methyl-2-buten-1-yl, and the like.

The term "$C_3$-$C_{12}$-cycloalkyl," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo [2.2.1] heptyl, and bicyclo [2.2.2] octyl.

It is understood that any alkyl, alkenyl, alkynyl and cycloalkyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

The terms "substituted aryl", "substituted heteroaryl," "substituted $C_1$-$C_6$ alkyl," or "substituted $C_1$-$C_{12}$ alkyl," "substituted $C_2$-$C_6$ alkenyl," "substituted $C_2$-$C_6$ alkynyl," "substituted $C_1$-$C_8$ alkylene," "substituted $C_2$-$C_8$ alkenylene," "substituted $C_2$-$C_8$ alkynylene," "substituted aliphatic," as used herein, refer to aryl, heteroaryl, $C_1$-$C_6$ alkyl, $C_1$-$C_{12}$ alkyl, $C_2$-$C_6$ alkenyl, $C_2$-$C_6$ alkynyl, $C_1$-$C_8$ alkylene, $C_2$-$C_8$ alkenylene, substituted $C_2$-$C_8$ alkynylene, aliphatic groups as previously defined, substituted by independent replacement of one, two, or three or more of the hydrogen atoms thereon with substituents including, but not limited to, —F, —Cl, —Br, —I, —OH, protected hydroxyl, —NO$_2$, —CN, —$C_1$-$C_{12}$-alkyl optionally substituted with, for example, halogen, $C_2$-$C_{12}$-alkenyl optionally substituted with, for example, halogen, —$C_2$-$C_{12}$-alkynyl optionally substituted with, for example, halogen, —NH$_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —CONH$_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —OCO$_2$—$C_1$-$C_{12}$-alkyl, —OCO$_2$—$C_2$-$C_{12}$-alkenyl, —OCO$_2$—$C_2$-$C_{12}$-alkenyl, —OCO$_2$—$C_3$-$C_{12}$-cycloalkyl, —OCO$_2$-aryl, —OCO$_2$-heteroaryl, —OCO$_2$-heterocycloalkyl, —OCONH$_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —NHCO$_2$—$C_1$-$C_{12}$-alkyl, —NHCO$_2$—$C_2$-$C_{12}$-alkenyl, —NHCO$_2$—$C_2$-$C_{12}$-alkenyl, —NHCO$_2$—$C_3$-$C_{12}$-cycloalkyl, —NHCO$_2$— aryl, —NHCO$_2$— heteroaryl, —NHCO$_2$—heterocycloalkyl, —NHC(O)NH$_2$, —NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)NH$_2$, —NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)

NH-heterocycloalkyl, —NHC(NH)NH$_2$, —NHC(NH)NH—C$_1$-C$_{12}$-alkyl, —NHC(NH)NH—C$_2$-C$_{12}$-alkenyl, —NHC(NH)NH—C$_2$-C$_{12}$-alkenyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_{12}$-alkenyl, —NHC(NH)—C$_2$-C$_{12}$-alkenyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkenyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkenyl, —S(O)—C$_3$-C$_{12}$-cycloalkyl, —S(O)-aryl, —S(O)-heteroaryl, —S(O)-heterocycloalkyl-SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkenyl, —SO$_2$NH—C$_3$-C$_{12}$-cycloalkyl, —SO$_2$NH— aryl, —SO$_2$NH-heteroaryl, —SO$_2$NH— heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S-heteroaryl, —S-heterocycloalkyl, or methylthiomethyl. It is understood that the aryls, heteroaryls, alkyls, and the like can be further substituted.

The term "alicyclic," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo [2.2.1] heptyl, and bicyclo [2.2.2] octyl. Such alicyclic groups may be further substituted.

The term "heterocyclic" as used herein, refers to a non-aromatic 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (iv) any of the above rings may be fused to a benzene ring, and (v) the remaining ring atoms are carbon atoms which may be optionally oxo-substituted. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted.

The term "halogen," as used herein, refers to an atom selected from fluorine, chlorine, bromine and iodine.

The term "hydroxy activating group", as used herein, refers to a labile chemical moiety which is known in the art to activate a hydroxyl group so that it will depart during synthetic procedures such as in a substitution or an elimination reactions. Examples of hydroxyl activating group include, but not limited to, mesylate, tosylate, triflate, p-nitrobenzoate, phosphonate and the like.

The term "activated hydroxy", as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the are described generally in T. H. Greene and P. G. M. Wuts, *Protective Groups in Organic Synthesis*, 3rd edition, John Wiley & Sons, New York (1999). Examples of hydroxylprotecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, paramethoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxylprotecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group", as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs Topical and Ocular Drug Delivery*, (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis*, 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

The term "protogenic organic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This invention also encompasses pharmaceutical compositions containing, and methods of treating bacterial infections through administering, pharmaceutically acceptable prodrugs of compounds of the formula I. For example, compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula I. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

As used herein, unless otherwise indicated, the term "bacterial infection(s)" or "protozoa infections"; includes, but is not limited to, bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections and disorders related to such infections include, but are not limited to, the following: pneumonia, otitis media, sinusitus, bronchitis, tonsillitis, cystic fibrosis (CF) and mastoiditis related to infection by *Streptococcus pneumoniae, Haemophilus influenzae, Moraxella catarrhalis, Staphylococcus aureus, Peptostreptococcus* spp., or *Pseudomonas* spp.; pharynigitis, rheumatic fever, and glomerulonephritis related to infection by *Streptococcus pyogenes*, Groups C and G streptococci, *Clostridium* diptheriae, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; uncomplicated skin and soft tissue infections, abscesses and osteomyelitis, and puerperal fever related to infection by *Staphylococcus aureus*, coagulase-positive staphylococci (i.e., *S. epidermidis, S. hemolyticus*, etc.), *S. pyogenes, S. agalactiae*, Streptococcal groups C-F (minute-colony streptococci), viridans streptococci, *Corynebacterium* spp., *Clostridium* spp., or *Bartonella henselae*; uncomplicated acute urinary tract infections related to infection by *S. saprophyticus* or *Enterococcus* spp.; urethritis and cervicitis; and sexually transmitted diseases related to infection by *Chlamydia trachomatis, Haemophilus ducreyi, Treponema pallidum, Ureaplasma urealyticum*, or *Nesseria gonorrheae*; toxin diseases related to infection by *S. aureus* (food poisoning and Toxic shock syndrome), or Groups A, S. and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *C. trachomatis, N. gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; gastroenteritis related to infection by *Campylobacter jejuni*; intestinal protozoa related to infection by *Cryptosporidium* spp. odontogenic infection related to infection by viridans streptococci; persistent cough related to infection by *Bordetella pertussis*; gas gangrene related to infection by *Clostridium perfringens* or *Bacteroides* spp.; Skin infection by *S. aureus, Propionibacterium* acne; atherosclerosis related to infection by *Helicobacter pylori* or *Chlamydia pneumoniae*; or the like.

Bacterial infections and protozoa infections and disorders related to such infections that may be treated or prevented in animals include, but are not limited to, the following: bovine respiratory disease related to infection by *P. haemolytica, P. multocida, Mycoplasma bovis*, or *Bordetella* spp.; cow enteric disease related to infection by *E. coli* or protozoa (i.e., coccidia, cryptosporidia, etc.), dairy cow mastitis related to infection by *S. aureus, S. uberis, S. agalactiae, S. dysgalactiae, Klebsiella* spp., *Corynebacterium*, or *Enterococcus* spp.; swine respiratory disease related to infection by *A. pleuropneumoniae, P. multocida*, or *Mycoplasma* spp.; swine enteric disease related to infection by *E. coli, Lawsonia intracellularis, Salmonella* spp., or *Serpulina hyodyisinteriae*; cow footrot related to infection by *Fusobacterium* spp.; cow metritis related to infection by *E. coli*; cow hairy warts related to Infection by *Fusobacterium necrophorum* or *Bacteroides nodosus*; cow pink-eye related to infection by *Moraxella bovis*, cow premature abortion related to infection by protozoa (i.e. neosporium); urinary tract infection in dogs and cats related to infection by *E. coli*; skin and soft tissue infections in dogs and cats related to infection by *S. epidermidis, S. intermedius*, coagulase neg. *Staphylococcus* or *P. multocida*; and dental or mouth infections in dogs and oats related to infection by *Alcaligenes* spp., *Bacteroides* spp., *Clostridium* spp., *Enterobacter* spp., *Eubacterium* spp., *Peptostreptococcus* spp., *Porphfyromonas* spp., *Campylobacter* spp., *Actinomyces* spp., *Erysipelothrix* spp., *Rhodococcus* spp., *Trypanosoma* spp., *Plasmodium* spp., *Babesia* spp., *Toxoplasma* spp., *Pneumocystis* spp., *Leishmania* spp., and *Trichomonas* spp. or *Prevotella* spp. Other bacterial infections and protozoa infections and disorders related to such infections that may be treated or prevented in accord with the method of the present invention are referred to in J. P. Sanford at al., "The Sanford Guide To Antimicrobial Therapy," 26th Edition, (Antimicrobial Therapy, Inc., 1996).

Antibacterial Activity

Susceptibility tests can be used to quantitatively measure the in vitro activity of an antimicrobial agent against a given bacterial isolate. Compounds are tested for in vitro antibacterial activity by a micro-dilution method. Minimal Inhibitory Concentration (MIC) is determined in 96 well microtiter plates utilizing the appropriate Mueller Hinton Broth medium (CAMHB) for the observed bacterial isolates. Antimicrobial agents are serially diluted (2-fold) in DMSO to produce a concentration range from about 64 µg/ml to about 0.03 µg/ml. The diluted compounds (2 µl/well) are then transferred into sterile, uninoculated CAMHB (0.2 mL) by use of a 96 fixed tip-pipetting station. The inoculum for each bacterial strain is standardized to $5 \times 10^5$ CFU/mL by optical comparison to a 0.5 McFarland turbidity standard. The plates are inoculated with 10 µl/well of adjusted bacterial inoculum. The 96 well plates are covered and incubated at 35+/−2° C. for 24 hours in ambient air environment. Following incubation, plate wells are visually examined by Optical Density measurement for the presence of growth (turbidity). The lowest concentration of an antimicrobial agent at which no visible growth occurs is defined as the MIC. The compounds of the invention generally demonstrated an MIC in the range from about 64 µg/ml to about 0.03 µg/ml.

All in vitro testing follows the guidelines described in the Approved Standards M7-A4 protocol, published by the National Committee for Clinical Laboratory Standards (NCCLS).

The invention further provides compositions and methods of treating patients suffering from an inflammatory condition comprising administering to a patient in need thereof, a therapeutically effective amount of at least one compound of the invention. Specific examples of inflammatory conditions treatable according to the invention include, but are not limited to, scleritis; epi-scleritis; allergic conjunctivitis; pulmonary inflammatory diseases, particularly CF, asthma, chronic obstructive pulmonary disease (COPD), allergic bronchopulmonary aspergillosis (ABPA), and sarcoidosis; procto-sigmoiditis; allergic rhinitis; arthritis; tendonitis; apthous stomatitis; and inflammatory bowel disease.

The invention further provides compositions and methods for i) prophylactic treatment of those patients susceptible to the symptoms CF including pulmonary infection and inflammation associated with CF, ii) treatment at the initial onset of symptoms of pulmonary infection and inflammation associated with CF, and iii) treatment of ongoing or relapsing symptoms of infection and inflammation associated with CF. In accordance with the invention a compound of the invention, is administered to a patient in need of treatment for CF, in amount sufficient to prevent, diminish or eradicate symptoms of CF including chronic pulmonary inflammation and infection.

Pharmaceutical Compositions.

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43,650 by Montgomery, all of which are incorporated herein by reference). A discussion of pulmonary delivery of antibiotics is also found in U.S. Pat. No. 6,014,969, incorporated herein by reference.

According to the methods of treatment of the present invention, bacterial infections, cystic fibrosis and inflammatory conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically exipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The pharmaceutical compositions of this invention can be administered orally to fish by blending said pharmaceutical compositions into fish feed or said pharmaceutical compositions may be dissolved in water in which infected fish are placed, a method commonly referred to as a medicated bath. The dosage for the treatment of fish differs depending upon the purpose of administration (prevention or cure of disease) and type of administration, size and extent of infection of the fish to be treated. Generally, a dosage of 5-1000 mg, preferably 20-100 mg, per kg of body weight of fish may be administered per day, either at one time or divided into several times. It will be recognized that the above-specified dosage is only a general range which may be reduced or increased depending upon the age, body weight, condition of disease, etc. of the fish.

Unless otherwise defined, all technical and scientific terms used herein are accorded the meaning commonly known to one of ordinary skill in the art. All publications, patents, published patent applications, and other references mentioned herein are hereby incorporated by reference in their entirety.

Abbreviations

Abbreviations which may be used in the descriptions of the scheme and the examples that follow are:

Ac for acetyl;
AIBN for azobisisobutyronitrile;
$Bu_3SnH$ for tributyltin hydride;
CDI for carbonyldiimidazole;
dba for dibenzylidene acetone;
dppb for diphenylphosphino butane;
DBU for 1,8-diazabicyclo[5.4.0]undec-7-ene;
DEAD for diethylazodicarboxylate;
DMAP for dimethylaminopyridine;
DMF for dimethyl formamide;
DPPA for diphenylphosphoryl azide;
EtOAc for ethyl acetate;
MeOH for methanol;
Ms for mesylate or $O-SO_2-CF_3$;
$NaN(TMS)_2$ for sodium bis(trimethylsilyl)amide;

NMMO for N-methylmorpholine N-oxide;
TEA for triethylamine;
THF for tetrahydrofuran;
TPP or PPh₃ for triphenylphosphine;
MOM for methoxymethyl;
Boc for t-butoxycarbonyl;
Bz for benzoyl;
Bn for benzyl;
Ph for phenyl;
POPd for dihydrogen dichlorobis(di-tert-butylphosphinito-KP)palladate(II);
TBS for tert-butyl dimethylsilyl; or
TMS for trimethylsilyl.

Synthetic Methods

The compounds and processes of the present invention will be better understood in connection with the following synthetic schemes that illustrate the methods by which the compounds of the invention may be prepared.

In accordance with Scheme 1, the 9-keto group of erythromycins can be initially converted into an oxime by methods described in U.S. Pat. No. 4,990,602, followed by removal of the cladinose moiety of the macrolide of formula (1-1) either by mild acid hydrolysis or by enzymatic hydrolysis to afford compounds of formula (1-2). Representative acids include, but are not limited to, dilute hydrochloric acid, sulfuric acid, perchloric acid, chloroacetic acid, dichloroacetic acid or trifluoroacetic acid. Suitable solvents for the reaction include, but are not limited to, methanol, ethanol, isopropanol, butanol, water and mixtures there of. Reaction times are typically 0.5 to 24 hours. The reaction temperature is preferably 0-80° C.

The 2'-hydroxyl and the oxime groups are protected by reaction with suitable hydroxyl protecting reagents. Typical hydroxylprotecting reagents include, but are not limited to, acetylating agents, silylating agents, ortho formate, acid anhydrides, and the like. A more thorough discussion of

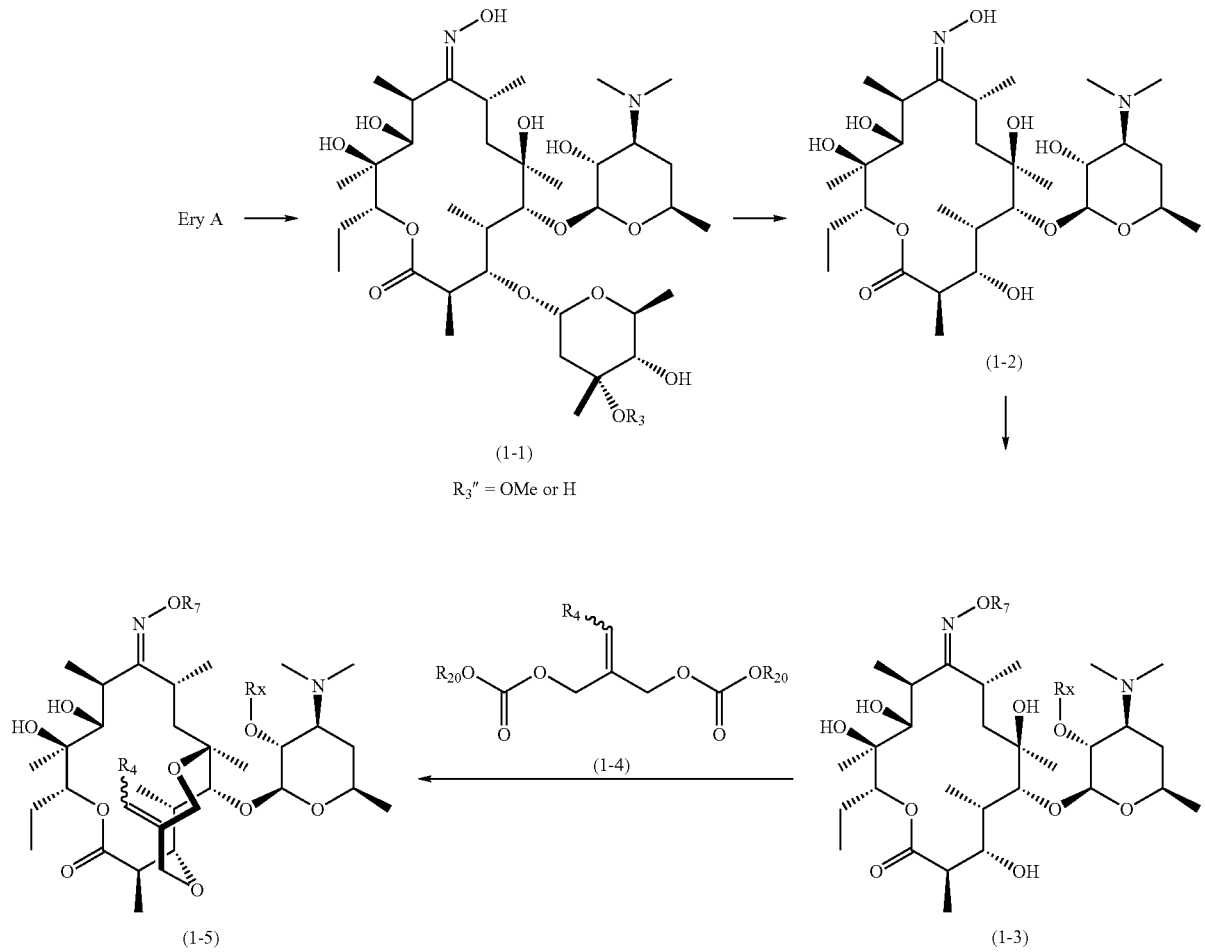

A process of the invention, as illustrated in Scheme 1, involves preparing a compound of formula (1-5) by reacting a compound of formula (1-3) with a suitable alkylating agent.

solvents and conditions for protecting the hydroxyl group can be found in T. W. Greene and P. G. M. Wuts, *Protective Groups in Organic Synthesis*, 3$^{rd}$ ed., John Wiley & Son, Inc, 1999. Acetylation of the hydroxyl group is typically accomplished by treating the compound (1-2) with an acetylating reagent such as acetic anhydride to give compound of formula (1-3).

The erythromycin derivative of formula (1-3) is then reacted with an alkylating agent of the formula:

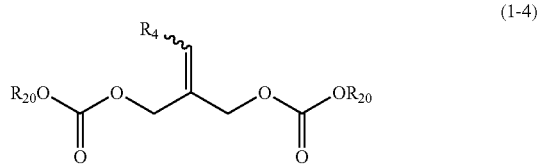

(1-4)

wherein $R_4$ is as previously defined and $R_{20}$ is $—C_1-C_{12}$ alkyl, $—C_1-C_{12}$ alkenyl, or $—C_1-C_{12}$ alkynyl optionally substituted with one or more substitutents selected from halogen, aryl, substituted aryl, heteroaryl, or substituted heteroaryl; $—C_3-C_{12}$ cycloalkyl.

Most palladium (0) catalysts are expected to work in this process. Some palladium (II) catalysts, such as palladium (II) acetate, which is converted into a palladium (0) species in-situ by the actions of a phosphine, will work as well. See, for example, Beller et al. *Angew. Chem. Int. Ed. Engl.*, 1995, 34 (17), 1848. The palladium catalyst can be selected from, but not limited to, palladium (II) acetate, tetrakis(triphenylphospine)palladium (0), tris(dibenzylideneacetone)dipalladium, tetradibenzylideneacetone)dipalladium and the like. Palladium on carbon and palladium (II) halide catalysts are less preferred than other palladium catalysts for this process.

Suitable phosphines include, but are not limited to, triphenylphosphine, bis(diphenylphosphino)methane, bis(diphenylphosphino)ethane, bis(diphenylphosphino)propane, 1,4-bis(diphenylphosphino)butane, bis(diphenylphosphino)pentane, and tri-o-tolyl-phosphine, and the like. The reaction is carried out in an aprotic solvent, preferably at elevated temperature, preferably at or above 50° C. Suitable aprotic solvents include, but are not limited to, tetrahydrofuran, N,N-dimethylformamide, dimethyl sulfoxide, N-methyl-2-pyrrolidone, toluene, hexamethylphosphoric triamide, 1,2-dimethoxyethane, methyl-tert-butyl ether, heptane, acetonitrile, isopropyl acetate and ethyl acetate.

Generally, the alkylating agents have the formula (1-4) as previously described. The preferred alkylating agents are those wherein $R_{20}$ is tert-butyl, isopropyl or isobutyl. The alkylating reagents are prepared by reaction of a diol with a wide variety of compounds for incorporating the di-carbonate moiety. The compounds include, but are not limited to, tert-butyl chloroformate, di-tert-butyl dicarbonate, and 1-(tert-butoxycarbonyl)imidazole and the reaction is carried out in the presence of an organic or an inorganic base. The temperature of the reaction varies from about −30° C. to approximately 30° C.

Scheme 2

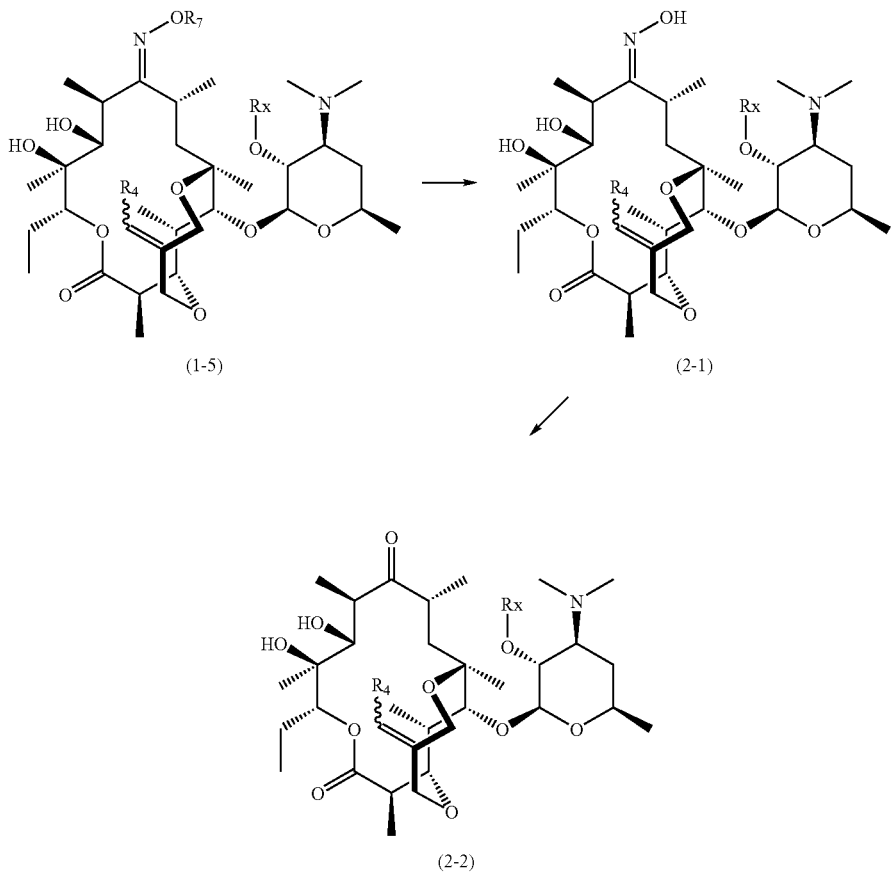

Scheme 2 outlined the synthesis of intermediate (2-2). Selective deprotection of the oxime is typically accomplished via alkaline hydrolysis in protic solvents. Representative alkali include lithium hydroxide, sodium hydroxide, potassium hydroxide, and the like. Solvents which are applicable include but are not limited to tetrahydrofuran, 1,4-dioxane, 1,2-dimethoxyethane, isopropanol, ethanol, butanol, water and mixtures thereof. The reaction temperature is preferably 0° to 35° C. and reaction time is preferably 0.5 to 24 hours.

In a like fashion, simultaneous deprotection of both the oxime and the 2' hydroxyl can be accomplished under a variey of conditions. Conditions for deprotection include, but are not limited to, treating with an alcoholic solvent at from room temperature to reflux, or treatment with a primary amine, such as butylamine. Alcoholic solvents preferred for the deprotection are methanol and ethanol. A more thorough discussion of the procedures, reagents and conditions for removing protecting groups is described in the literature, for example, by T. W. Greene and P. G. M. Wuts in "Protective hydrolysis by aqueous alcohol at elevated temperature to give compounds of formula (2-2). Many reducing agents can be used to effect this transformation including, but not limited to: lithium aluminum hydride, titanium trichloride, sodium nitrite, sodium thiosulfate, sodium cyanoborohydride, borane, and various sulfides such as sodium hydrogen sulfide, sodium ethoxide. For a more detailed account of oxime reduction see J. March in "Advanced Organic Chemistry" 4$^{th}$ ed., Wiley & Son, Inc, 1992, which is incorporated by reference herein.

A particularly useful method for the reduction of oximes to the corresponding imine uses a sulfite reducing agent, such as sodium nitrite, sodium hydrogensulfite or titanium trichloride under acidic conditions, typically in protic solvents. Representative acids include, but are not limited to, acetic acid, formic acid, dilute hydrochloric acid, dilute phosphoric acid, dilute sulfuric acid, and the like. Protic solvents include, but are not limited to, mixtures of water and methanol, ethanol, isopropanol, or butanol. The reaction is typically carried out at 25° to 110° C., preferably for between 1 and 10 hours.

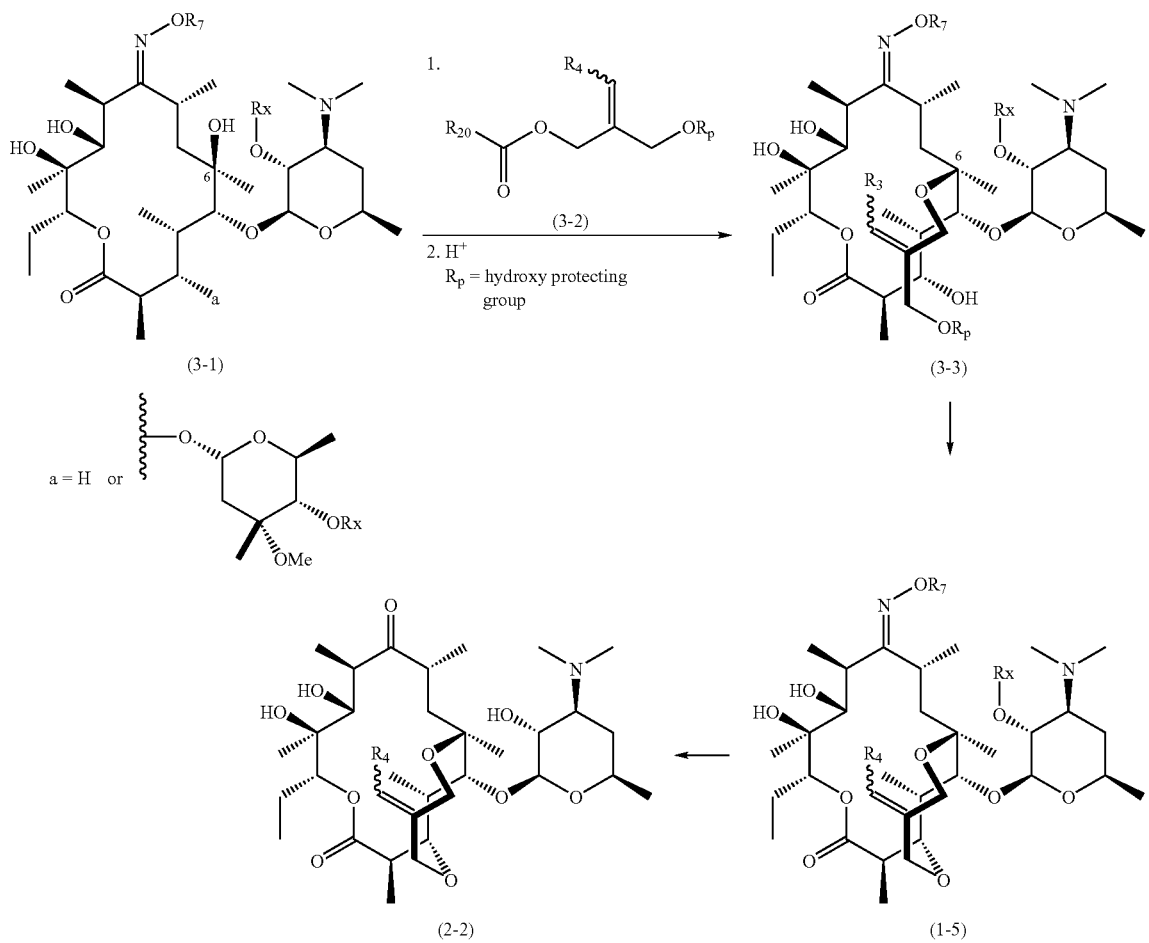

Groups in Organic Synthesis" 3$^{rd}$ ed., John Wiley & Son, Inc, 1999, referred to above herein.

Deoxygenation of compounds of formula (2-1) under reducing conditions gives the resulting imine followed by Alternatively, ketone (2-2) can also be prepared via a stepwise process as shown in Scheme 3. The initial step is the alkylation of the 6-hydroxy moiety of intermediate (3-1) with alkylating agents of formula (3-2), wherein $R_{10}$ are as previously defined and $R_p$ is hydroxylprotecting group, in the presence of Pd(0) as previously described in Scheme 1, followed by the removal of the cladinose moiety of formula (3-1) (if E is a cladinose) with either mild acid hydrolysis or by enzymatic hydrolysis to yield compounds of formula (3-3). Representative acids include dilute hydrochloric acid, sulfuric acid, perchloric acid, chloroacetic acid, dichloroacetic acid or trifluoroacetic acid. Suitable solvents for the reaction include methanol, ethanol, isopropanol, butanol, water and mixtures there of. Reaction times are typically 0.5 to 24 hours. The reaction temperature is preferably 0 to 80° C. Compounds of formula (3-3) can be converted to the cyclized products (1-5) via manipulation of $R_p$ to the C(O)OR$_{10}$, where $R_p$ and $R_{20}$ are as previously defined, subsequently by intramolecular cyclization in the presence of Pd(0) as previously described in Scheme 1. Finally, conversion of compounds of formula (1-5) to ketone (2-2) is as previously outlined in scheme 2.

The synthesis of compounds of formula (4-6) is outlined in scheme 4. Compounds of formula (4-2) can be obtained by treating compounds of fromula (4-1) with ethylenecarbonate in refluxing triethylamine as described for example in Elliott et al., *J. Med. Chem.*, 1998, 41, 1651-1659 or by treating with ethylenecarbonate and a base such as, but not limited to, potassium carbonate in hot DMF, preferably at 110° C. The hydroxy group at position 12 of compounds of formula (4-2) is esterified by treatment with an appropriate carboxylic acid (4-4), and coupling reagents such as, but not limted to, DCC and DMAP with appropriate chorinated solvent such as, but not limited to, methylene chloride. Depending on the nature of W, compounds of formula (4-5) can also be synthesized via a two step procedure where the hydroxy group at the 12 position is first reacted with 2-chloroacetic acid to give coumpounds of formula (4-3). The intermediate is then treated with the appropriate nucleophile WH in a suitable solvent such as, but not limited to,

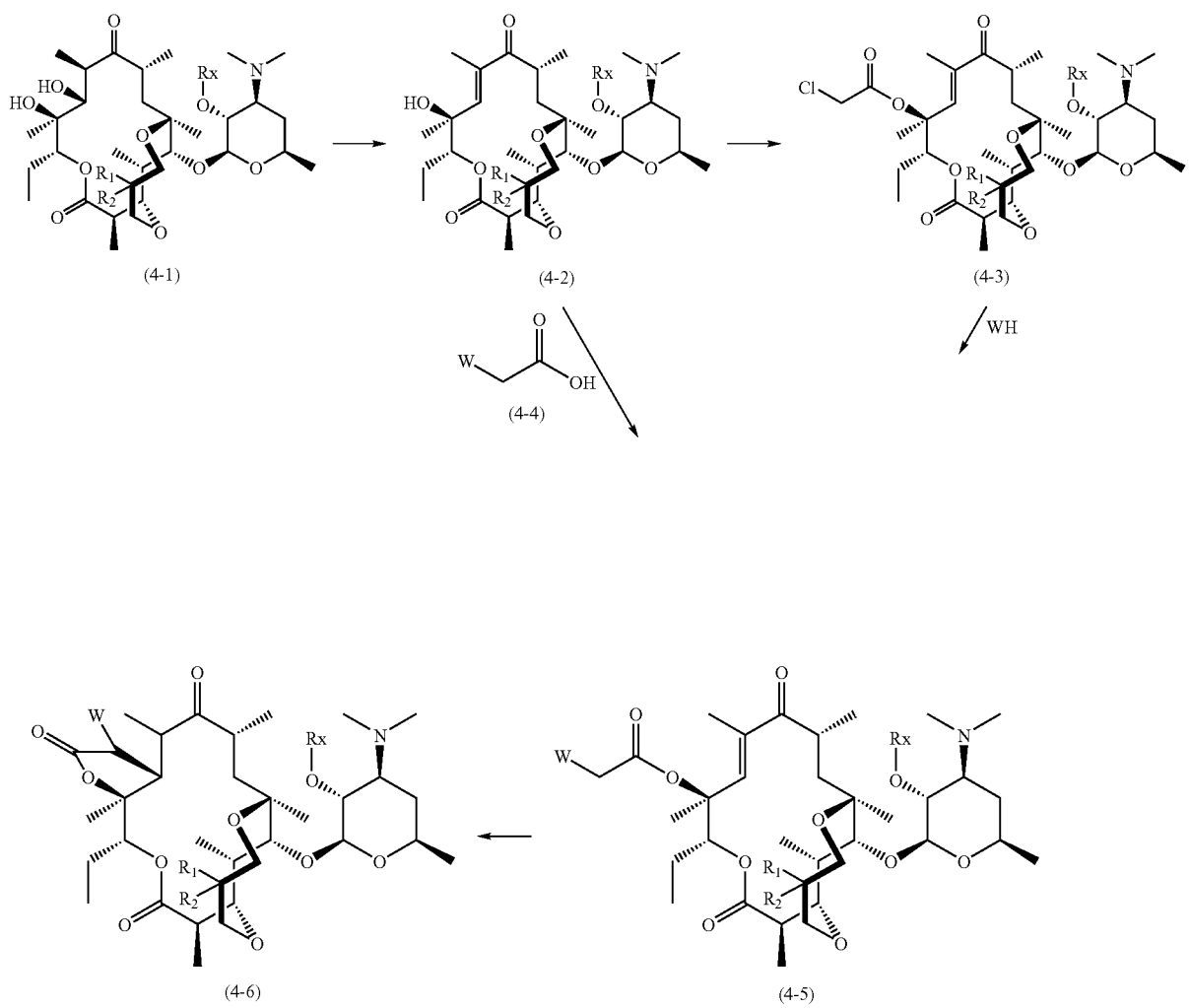

acetone and in the presence of base such as DBU. Compounds of formula (4-5) are treated with an alkali metal base such as, but not limited to, NaH or potassium tert-butoxide in an aprotic solvent such as DMF or THF to afford compounds of formula (4-6).

When W is a cyano moiety, compounds of formula (4-6) can be obtained directly in one step without the addition of any base from compounds of formula (4-3) and tetrabutylammonium cyanide.

acetonitrile at temperatures ranging from 25° C. to the boiling point of the solvent. After 1 hour benzylalcohol, p-methoxybenzylalcohol, t-butylalcohol, 2-trimethylsilylethanol or water is added and the mixutre is heated to temperatures ranging from 50° C. to 110° C. during 5 to 24 hours. Alternatively, compounds formula (5-2) is treated with ethyl chloroformate and triethylamine in a mixture of acetone and water at temperatures ranging from −5° C. to 10° C. preferably 0° C. during 1 to 2 hours. Sodium azide is

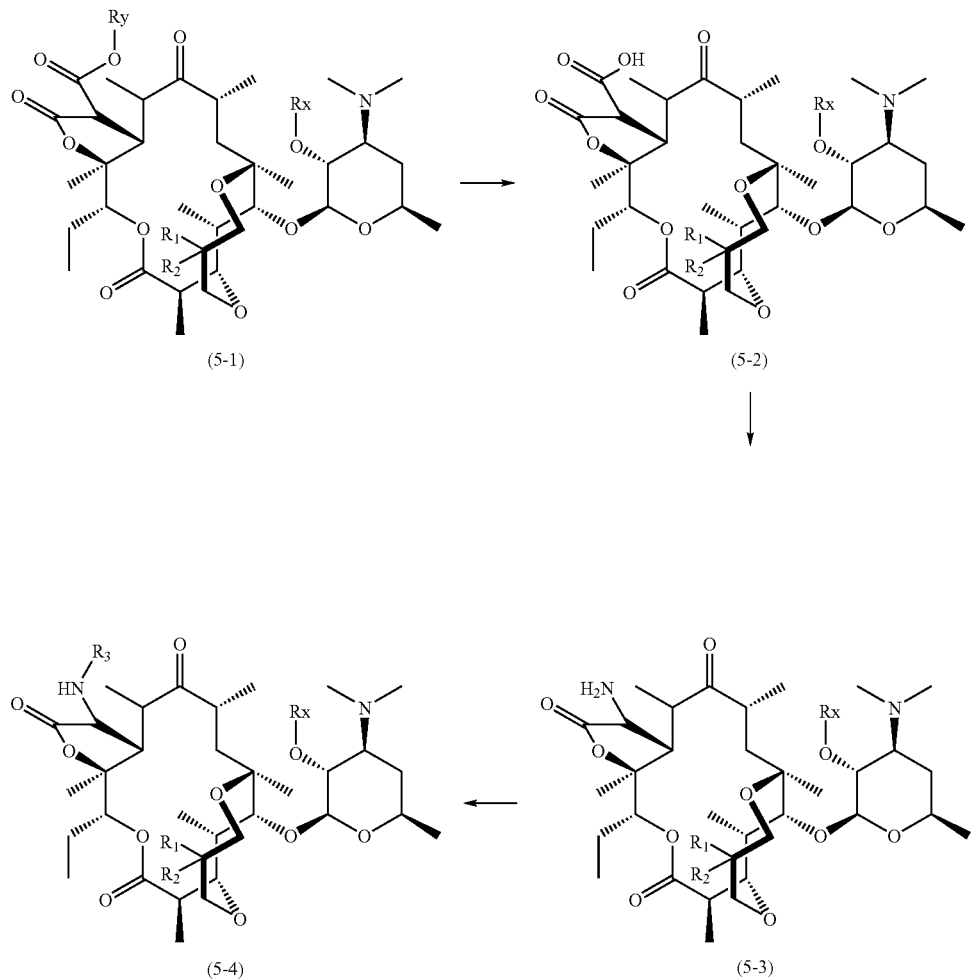

Scheme 5

Compounds of formula (5-1), where Ry is a carboxy protecting group and $R_1$, $R_2$ and Rx are previously defined, can be further elaborated as described in scheme 5. In the first step, deprotection of the carboxy group by methods well known in the art (see T. H. Greene and P. G. M. Wuts, *Protective Groups in Organic Synthesis*, 3rd edition, John Wiley & Sons, New York, 1999.) to give the corresponding acid (5-2) which are then subjected to the so called 'Curtius rearrangement' by reacting with diphenylphosphoryl azide and triethylamine in a solvent such as benzene, toluene or then added and the mixture is stirred for another 1 to 5 hours at the same temperature. If one of the above alcohols mentioned alcohols has been added to the reaction mixture, the free amine is liberated from the intermediate carbamate, depending on the nature the alcohol; with H2/Pd/C (in the case of benzylacohol or p-methoxybenzylalcohol), HCl or TFA (in the case of of t-butylalcohol) or tetrabutylammonium fluoride (in the case of 2-trimethylsilylethanol) according to standard procedures described in T. H. Greene and P. G. M. Wuts, *Protective Groups in Organic Synthesis*, 3rd edition, John Wiley & Sons, New York, 1999 to give the compounds of formula (5-3) as a mixture of diastereoisomers in various ratios. Compounds of formula (5-3) can be further elaborated to give compounds of formula (5-4) via methods known in the art of chemistry, such as akylation or acylation of the amino group with appropriate akylation or acylation groups.

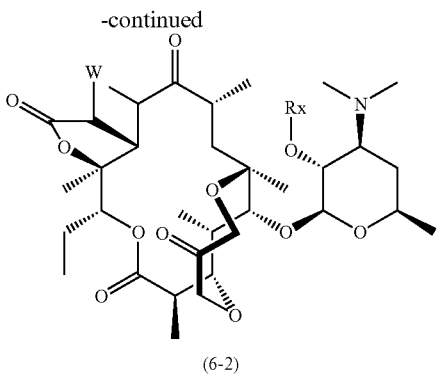

(6-2)

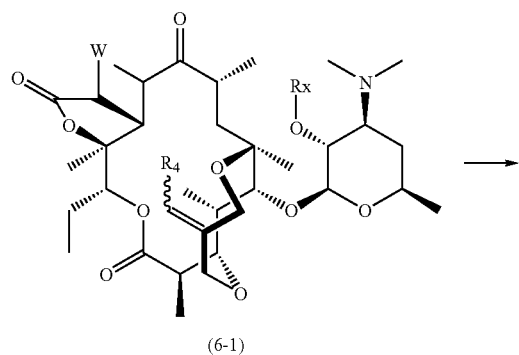

(6-1)

Scheme 5 illustrates another process of the invention by which to prepare compound of the present invention. Conversion of alkenes (6-1) into ketones (6-2) can be accomplished by ozonolysis followed by decomposition of the ozonide with the appropriate reducing agents. The reaction is typically carried out in an inert solvent such as, but not limited to, methanol, ethanol, ethyl acetate, glacial acetic acid, chloroform, methylene chloride or hexane or mixtures thereof, preferably methanol, preferably at −78° C. to −20° C. Representative reducing agents are, for example, triphenylphosphine, trimethylphosphite, thiourea, and dimethyl sulfide, preferably triphenylphosphine. A more thorough discussion of ozonolysis and conditions therefor may be found in J. March, *Advanced Organic Chemistry*, 4th ed., Wiley & Son, Inc, 1992. Alternatively, compounds of formula (6-1) can be prepared from compounds of formula (6-2) dihydroxydation with $OsO_4$ followed by $NaIO_4$ cleavage.

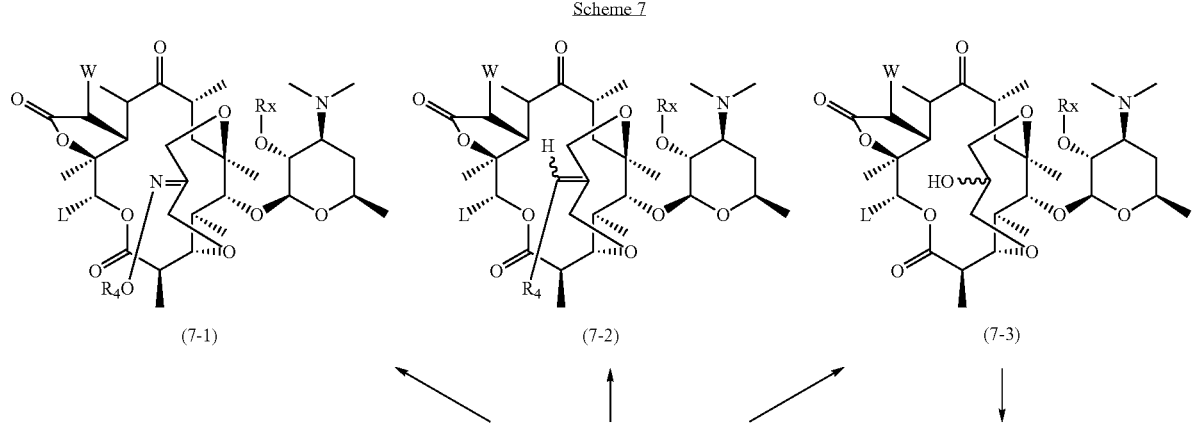

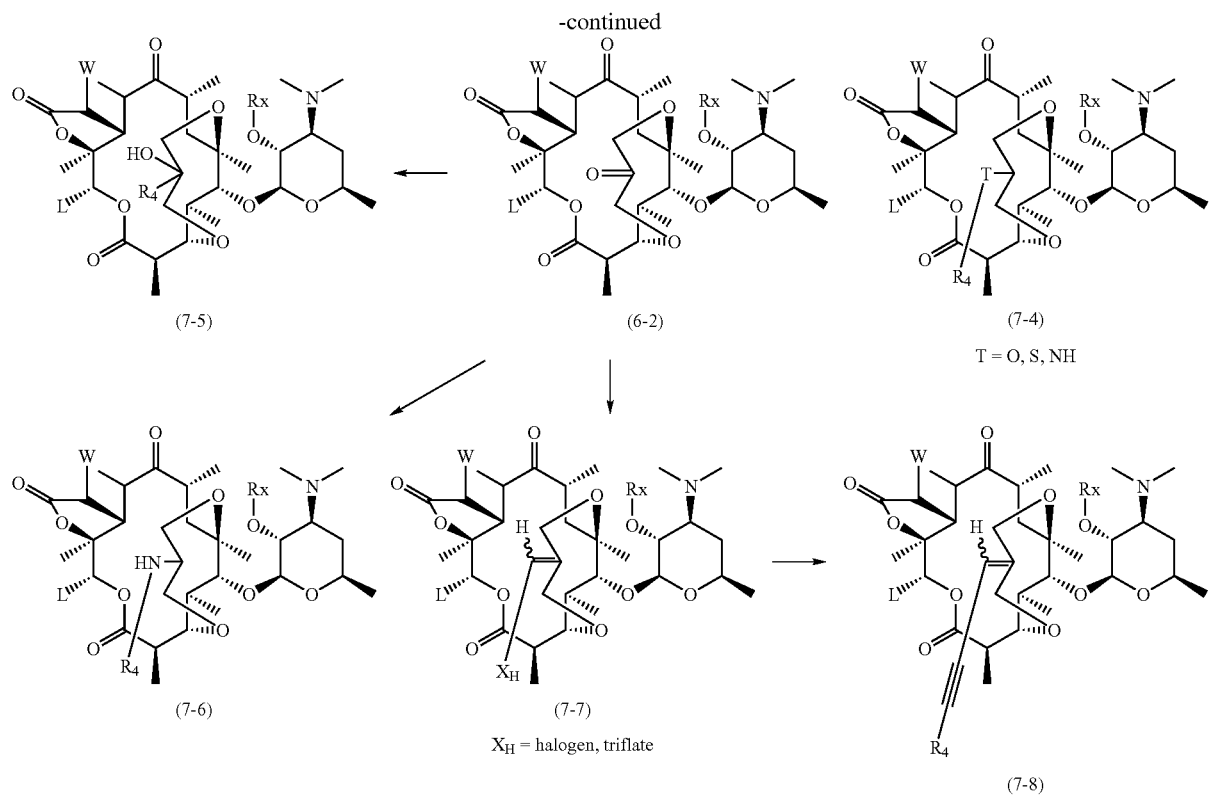

Compounds according to the invention of the formula (6-2) can be further functionalized in a variety of ways. Scheme 8 details a procedure for the conversion of the ketone of formula (7-2) into an oxime of formula (7-1). Oxime formation can be accomplished using the appropriate substituted hydroxylamine under either acidic or basic conditions in a variety of solvents. Representative acids include, but are not limited to, hydrochloric, phosphoric, sulfuric, p-toluenesulfonic, and pyridinium p-toluene sulfonate. Likewise, representative bases include, but are not limited to, triethylamine, pyridine, diisopropylethyl amine, 2,6-lutidine, and the like. Appropriate solvents include, but are not limited to, methanol, ethanol, water, tetrahydrofuran, 1,2-dimethoxyethane, and ethyl acetate. Preferably the reaction is carried out in ethanol using triethylamine as the base. The reaction temperature is generally 25° C. and reaction time is 1 to 12 hours.

It will be appreciated by one skilled in the art that ketones of formula (7-2) can be transformed into alkenes of formula (7-2) and (7-7) via Wittig reaction with the appropriate phosphonium salt in the presence of a base, see (a) Burke, *Tetrahedron Lett.*, 1987, 4143-4146, (b) Rathke and Nowak, *J. Org. Chem.*, 1985, 2624-2626, (c) Maryanoff and Reitz, *Chem. Rev.*, 1989, 863-927. Furthermore, vinyl halides of formula (7-7) can be functionalized by Sonogashira coupling with alkynes in the presence of a palladium catalyst, a copper halide and an amine base to give compounds of formula (7-8) (see (a) Sonogashira, *Comprehensive Organic Synthesis*, Volume 3, Chapters 2,4; (b) Sonogashira, *Synthesis* 1977, 777.). In a similar manner, alkenes of formula (7-2) can be obtained from vinyl halides (7-7) via Suzuki cross coupling with organoboron reagents in the presence of a palladium catalyst and a base, or via Stille cross coupling with organostananes in the presence of a palladium catalyst (see (a) Suzuki, *J. Organomet. Chem.* 1999, 576,147-168, (b) Stille, *Angew. Chem. Int. Ed. Engl.*, 1986, 508-524 (c) Farina, *J. Am. Chem. Soc.*, 1991, 9585-9595).

Furthermore, alcohols of type (7-3) can be prepared by reduction of the corresponding ketone of formula (6-2) under a variety of conditions (see Hudlicky, M. *Reductions in Organic Chemistry*, Ellis Horwood Limited: Chichester, 1984). The alcohols thus derived can be further modified to give compounds of formula (7-4). A process to generate compounds of formula (7-4) includes, but is not limited to, alkylation of the alcohol with an electrophile or conversion of the alcohol into a leaving group, such as a triflate, tosylate, phosphonate, halide, or the like, followed by displacement with a heteroatom nucleophile (e.g. an amine, alkoxide, sulfide or the like).

Yet another means by which to functionalize ketones of formula (6-2) is via addition of Grignard reagents to form alcohols of formula (7-5). The requisite Grignard reagents are readily available via the reaction of a variety of alkyl or aryl halides with magnesium under standard conditions (see B. S. Furniss, A. J. Hannaford, P. W. G. Smith, A. R. Tatchell, *Vogel's Textbook of Practical Organic Chemistry*, 5$^{th}$ ed., Longman, 1989). The addition is performed in an inert solvent, generally at low temperatures. Suitable solvents include, but are not limited to, tetrahydrofuran, diethylether, 1,4-dioxane, 1,2-dimethoxyethane, and hexanes. Preferably the solvent is tetrahydrofuran or diethylether. Preferably the reaction is run at −78° C. to 0° C.

In a similar way, reaction with other organometallic reagents gives rise to alcohols of formula (7-5). Examples of useful organometallic reagents include, but are not limited to, organo-aluminum, organo-lithium, organo-cerium, organo-zinc, organo-thallium, and organo-boron reagents. A more thorough discussion of organometallic reagents can be found in B. S. Furniss, A. J. Hannaford, P. W. G. Smith, A. R. Tatchell, *Vogel's Textbook of Practical Organic Chemistry*, 5$^{th}$ ed., Longman, 1989.

Ketone of formula (6-2) can be further utilized by conversion into amine of formula (7-6) via a reductive amination. Reductive amination is achieved by treating the ketone with an amine in the presence of a reducing agent to obtain the product amine (7-6). The reaction can be carried out either with or without added acid. Examples of acids that are commonly used include, but are not limited to, hydrochloric, phosphoric, sulfuric, acetic, and the like. Reducing agents that effect reductive amination include, but are not limited to, hydrogen and a catalyst, zinc and hydrochloric acid, sodium cyanoborohydride, sodium borohydride, iron pentacarbonyl, and alcoholic potassium hydroxide. Generally alcoholic solvents are used. The preferred conditions use sodium cyanoborohydride in methanol with added acetic acid.

It will be appreciated by one skilled in the art, that the unsaturated compounds represented by compounds (7-2) and (7-8) can be reduced to form the corresponding saturated compound (see Hudlicky, M., *Reductions in Organic Chemistry*, Ellis Horwood Limited: Chichester, 1984).

Compounds of the invention according to formula (8-1) are also capable of further functionalization to generate compounds of the present invention. Alkene (8-1) can be treated with an aryl halide or aryl triflate in the presence of a palladium catalyst [Pd(0) or Pd(II)] to provide compound (8-3): (See (a) Heck, *Palladium Reagents in Organic Synthesis*, Academic Press: New York, 1985, Chapter 1; (b) Sonogashira, *Comprehensive Organic Synthesis*, Volume 3, Chapters 2,4; (c) Sonogashira, *Synthesis* 1977, 777). Under the Heck coupling conditions, regioisomers and stereoisomers of the double bond are possible. Alternatively, compound (8-1) can undergo a cross metathesis reaction with vinylaromatic derivatives using ruthenium catalysts to give compounds of formula (7-2) (see (a) *J. Org. Chem.* 2000, 65, 2204-2207; (b) Reviews: *Synlett.* 1999, 2, 267; (c) Reviews: Ivin, K. J.; Mol, J. C., *Olefin Metathesis and Metathesis Polymerization*, 2$^{nd}$ ed., Academic Press: New York, 1997; (d) *J. Org. Chem.* 1999, 64, 4798-4816; (e) *Angew. Chem., Int. Ed. Engl.* 1997, 36, 2036-2056; (f) *Tetrahedron* 1998, 54, 4413-4450).

All references cited herein, whether in print, electronic, computer readable storage media or other form, are expressly incorporated by reference in their entirety, includ-

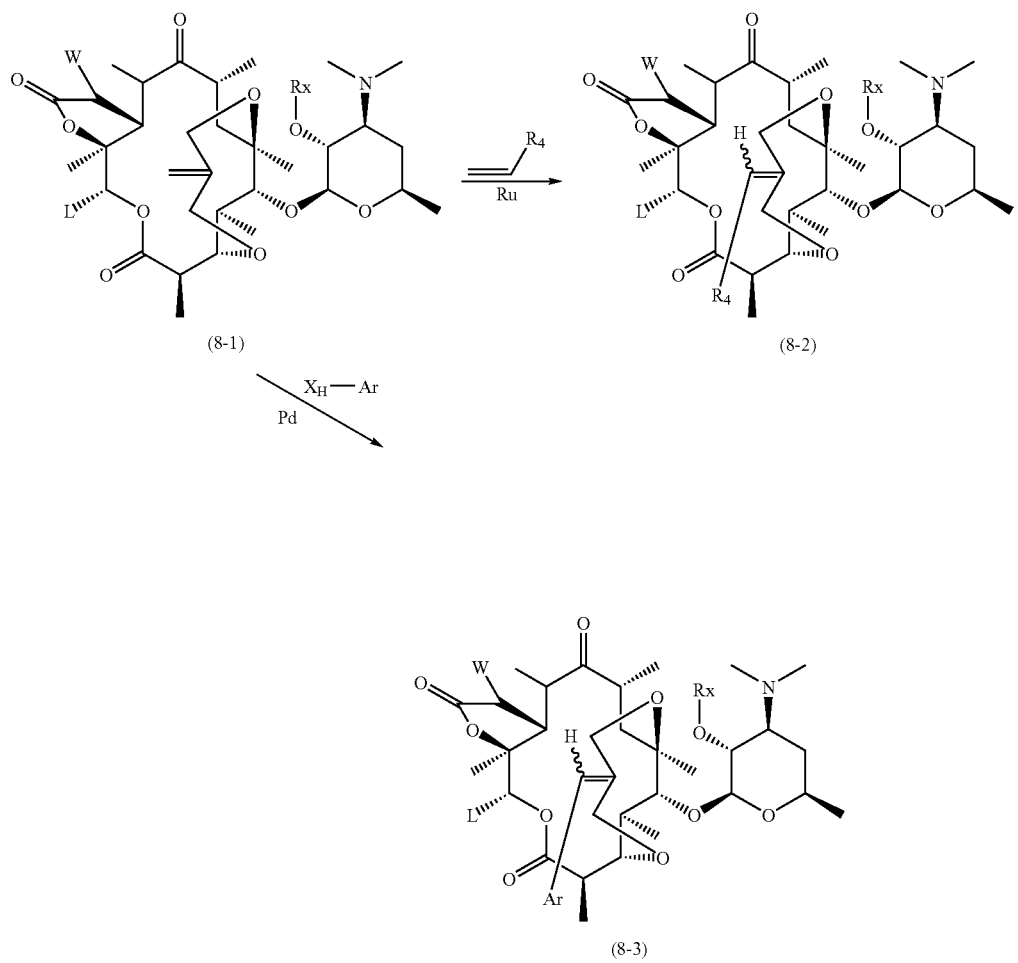

ing but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Compound of Formula V, wherein $R_1$ and $R_2$ Taken Together with the Carbon Atom to which They are Attached are $C=CH_2$, $W=[-S(CH_2)_2Ph]$ and $Rx=Ac$.

Step 1a.

To a flask containing a solution of commercially available Ery A oxime (1 eq.) in MeOH was slowly bubbled in anhydrous HCl gas (3.1 eq.) at 20 to 30° C. for 2 hrs. After HCl gas bubbling stops, the reaction mixture was stirred for 1 hr at room temperature. The mixture was then concentrated to about half the volume, and then quenched with dilute HCl solution. The resulting solution was extracted 4 times with dichloromethane. The aqueous solution was then basified with aqueous potassium carbonate solution until pH 9.5 to 10. The mixture was extracted 4 times with dichloromethane. The combine organic extracts were washed once with water, and then evaporated to dryness. The product was carried directly for the next step without further purification.

MS (ESI): m/z=591 [M+H].

Step 1b.

A solution of the compound from step (1a) in THF (12 L) was concentrated to a remaining volume about 9 L to azeotropically dry the material before acetylation reaction. To this clear THF solution was charged triethylamine (3.0 eq.), and then slowly charged $Ac_2O$ (2.3 eq.) at 20-30° C. over the period of about 30 min. Upon the completion of the addition, the reaction mixture was agitated at 25° C. for additional 3 hours. The reaction was diluted with EtOAc, subsequently washed 4 times with saturated aqueous $NaHCO_3$ solution, and 4 times with water. The organic solution was evaporated to dryness to afford the desired crude product which was purified by crystallization with EtOAc/Hex.

MS (ESI): m/z=675 [M+H].

Step 1c.

To a cloudy solution of compound from step (1b) in toluene was added carbonic acid 2-tert-butoxycarbonyloxymethyl-allyl ester tert-butyl ester (1.6 eq.) (prepared according to patent WO 03/097659 A1). The resulting mixture was degassed 3 times at 33° C. before $Pd_2(dba)_3$ (4 mol %) and dppb (8 mol %) were added and the resulting mixture was heated to reflux for 5 hours. After this time, the reaction was cooled back to room temperature and was concentrated under vacuo. The residue was passed through a short silica gel column eluting with 100% EtOAc to 95:5 (EtOAc:acetone) to give and the eluted product was concentrated and crystallized out from EtOAc to give the desired target.

MS (ESI): m/z 627.37 [M+H].

$^{13}C$ NMR (CDCl$_3$, ppm) δ: 176.8, 171.3, 170.2, 168.0, 143.0, 118.9, 102.3, 81.0, 80.0, 77.6, 75.0, 74.4, 72.3, 71.9, 70.6, 69.2, 63.55, 63.47, 60.6, 43.6, 42.7, 40.9, 37.9, 34.9, 31.0, 28.5, 22.9, 22.1, 21.6, 21.3, 21.2, 20.0, 18.9, 16.9, 15.1, 14.4, 12.2, 10.6, 10.5.

Step 1d.

A suspension of compound from step (1c) in methanol and was heated to reflux for 2.5 hours. The mixture was then cooled and evaporated to dryness. The white solid residue was carried directly for the next step without further purification.

MS (ESI): m/z 643.33 [M+H].

$^{13}C$ NMR (CDCl$_3$, ppm) δ: 177.3, 170.2, 144.7, 116.9, 104.5, 81.2, 81.0, 75.6, 75.0, 72.6, 71.2, 70.9, 69.6, 66.0, 64.2, 43.8, 42.8, 40.5, 38.3, 33.8, 28.8, 25.8, 22.7, 22.0, 21.4, 19.2, 16.6, 15.0, 12.1, 10.9, 10.8.

Step 1e.

To a stirred solution of compound from step (1d) (22 mmol) in ethanol was slowly added water (75 ml). To this mixture was added $NaNO_2$ (5 eq.) in one portion and then it was slowly treated with 1N aqueous HCl (110 ml). The reaction temperature was warmed to 70° C. over 20 min and was allowed to stir at this temperature for 2 hours. After the solution was cooled back to room temperature, it was basified with saturated $NaHCO_3$ to a pH of 9-10 and then extracted 5 times with dichloromethane. The combined organic extracts were washed once with brine, dried over $MgSO_4$, filtered and concentrated. The residue was purified by crystallization to afford the desired product.

MS (ESI): m/z 628.09 [M+H].

$^{13}C$ NMR (CDCl$_3$, ppm) δ: 220.6, 177.0, 143.9, 118.3, 104.5, 81.4, 80.7, 75.3, 75.1, 72.6, 70.8, 69.70, 69.66, 66.0, 63.7, 45.2, 43.7, 42.7, 40.5, 38.8, 38.5, 28.6, 22.7, 22.2, 21.4, 18.8, 16.6, 12.3, 12.1, 10.9, 10.6.

Step 1f.

To a solution of compound from step (1e) in $CH_2Cl_2$ was added $Ac_2O$ (1.2 eq.). The resulting solution was stirred at room temperature for 2.5 hours before it was diluted with EtOAc, washed 2 times with saturated $NaHCO_3$, once with brine, dried over $MgSO_4$ and concentrated under vacuum to give a white solid.

MS (ESI): m/z 670.10 [M+H].

$^{13}C$ NMR (CDCl$_3$, ppm) δ: 220.6, 176.9, 170.1, 143.8, 118.3, 102.4, 80.8, 80.5, 75.3, 75.1, 72.6, 72.0, 69.7, 69.3, 63.8, 63.5, 45.0, 43.6, 42.7, 40.9, 38.7, 38.4, 30.9, 22.8, 22.2, 21.6, 21.2, 18.7, 16.9, 12.2, 12.1, 10.7, 10.6.

Step 1g.

To a solution of compound from step (1f), ethylene carbonate (5.7 eq.) and triethylamine is heated to reflux overnight. Another 3.4 equivalent of ethylene carbonate is added to the mixture and is allowed to be stirred at reflux for an additional 18 hours. Excess triethylamine is removed in vacuo and water/10% HCl/EtOH (4:2:0.5) and the mixutre is further stirred at room temperature overnight. The reaction is then basified with 10% aqueous NaOH to pH 12-14 to precipitate the crude product, the aqueous layer is decanted, and the precipitate is dissolved in EtOAc, washed with saturated $NaHCO_3$, water and dried over $MgSO_4$, and concentrated to afford the desired product.

Step 1h.

To a solution of compound from step (1g), [[2-phenylethyl]thio]acetic acid (3.0 eq.) (prepared according to Weissbach et al., *Chem. Ber.* 1929, 62, 2423) and DMAP in $CH_2Cl_2$ under nitrogen is added a solution of DCC (3.0 eq.) in $CH_2Cl_2$ dropwise. Following addition, the solution is stirred at room temperature for 12 hours. The mixture is then poured in to 0.5 M $KH_2PO_4$ solution and extracted with $CH_2Cl_2$. The organic layer is washed with brine, dried over $Na_2SO_4$ and evaporated. The resulting residue is purified by flash column chromatography.

MS (ESI): m/z 652.36 [M+H].

Step 1i.

To an ice cold solution of compound from step 1h of Example 1 in dry DMF under nitrogen is added dropwise 1M solution of potassium tert-butoxide in THF. The resulting mixture is stirred at 0° C. for 1 hour and is then partitioned between diethylether and 0.5 M $KH_2PO_4$ solution. The organic layer was washed with 3% $NaHCO_3$ solution and brine, dried over $Na_2SO_4$ and evaporated. The crude mixture is purified by flash column chromatography to give a mixture of two diastereomers.

Example 2

Compound of Formula V, wherein $R_1$ and $R_2$ Taken Together with the Carbon Atom to which They are Attached are C=$CH_2$, W=[—S($CH_2$)$_2$Ph] and Rx=H A solution of compound from Example 1 in MeOH was stirred at room temperature overnight, the mixture was then concentrated to dryness and the residue was purified by column chromatography eluting with 2-5% 2N $NH_3$/MeOH in dichloromethane.

Example 3

Compound of Formula V, wherein $R_1$ and $R_2$ Taken Together with the Carbon Atom to which They are Attached are C=$CH_2$, W=$CO_2$Me, and Rx=Ac Step 3a.

To a solution of compound from step 1g of Example 1 in anhydrous toluene and pyridine methylmalonyl chloride was added at room temperature. After stirring for 1.5 hours, water was added. The organic layer was washed with brine, dried, filtered and concentrated under vacuum to give a yellow foam. The residue was purified by quick filtration through a filter of silica gel to afford the title compound.

MS (ESI): m/z 752.72 [M+H].

Step 3b.

A solution of compound from Step 3a in water, acetonitrile and DBU was stirred at room temperature for 3 days. After evaporating the solvent under reduced pressure, the residue was dissolved in methylene chloride and washed with water. The organic phase was washed with brine, dried, filtered and concentrated under vacuum to give the title compound.

MS (ESI): m/z 752.69 [M+H].

Example 4

Compound of Formula V, wherein $R_1$ and $R_2$ Taken Together with the Carbon Atom to which They are Attached are C=$CH_2$, W=H and Rx=Ac A stirred mixture of the title compound from Example 3 and lithium chloride in DMF was heated at 135° C. for 6 hours. The reaction mixture was allowed to reach room temperature; saturated aqueous $NaHCO_3$ solution was added and extracted with EtOAc. The combined organic extracts were washed with brine, dried, filtered and concentrated under vacuum to give the title compound.

MS (ESI): m/z 694.65 [M+H].

Example 5

Compound of Formula V wherein $R_1$ and $R_2$ Taken Together with the Carbon Atom to which They are Attached are C=$CH_2$, and W=Rx=H A solution of title compound from Example 4 in MeOH was stirred at 50° C. for 2.5 hours, the mixture was then concentrated to dryness and the residue was purified by column chromatography eluting with 2-5% 2N $NH_3$/MeOH in dichloromethane.

MS (ESI): m/z 652.64 [M+H].

$^{13}$C NMR (CDCl$_3$, ppm): 218.1, 177.2, 175.5, 146.8, 110.5, 105.6, 87.4, 83.5, 81.2, 80.64, 80.55, 73.8, 70.7, 69.9, 66.0, 64.3, 45.4, 43.1, 40.5, 39.0, 37.3, 29.9, 28.5, 24.3, 21.8, 21.5, 17.42, 17.38, 11.7, 10.9, 10.8.

Example 6

Compound of Formula V, wherein $R_1$ and $R_2$ Taken Together with the Carbon Atom to which They are Attached are C=O, and W=Rx=H To a solution of the title compound from Example title compound from Example 5 in acetone was added NaIO$_4$(s) (2.2 eq.) and then water. To this mixture was then added 4% wt. solution of OSO$_4$ in water (12 mol %) dropwise at room temperature. White precipitates were formed as reaction progressed. After 1.5 hours, the mixture was quenched with saturated NaHCO$_3$ and extracted with EtOAc. The combined organic extracts were dried over Na$_2$SO$_4$, filtered and concentrated under vacuum to give the title compound.

MS (ESI): m/z 654.59 [M+H].

Example 7

Compound of Formula V, wherein $R_1$ and $R_2$ Taken Together with the Carbon Atom to which They are Attached are C=NO[6'-amino-[2,2']bipyridinyl-6-ylmethyl], Rx=W=H To a solution of O-(6'-amino-[2,2']bipyridinyl-6-ylmethyl)-hydroxylamine (prepared according to literature procedure) (1.9 eq.) and 1M HCl (2.2 eq.) in EtOH was added title compound from Example 6 (0.14 mmol) in acetonitrile dropwise at room temperature. Solution turned slightly brown with some precipitate. After stirring for 30 min at room temperature the mixture was quenched with saturated NaHCO$_3$ and extracted with EtOAc. The combined organic extracts were washed with brine, dried, filtered and concentrated under vacuum to give the title compound as an E and Z oxime mixture.

MS (ESI): m/z 852.79 [M+H], 426.90 [M+2H].

Examples (8)-(179) of the Formula (A):

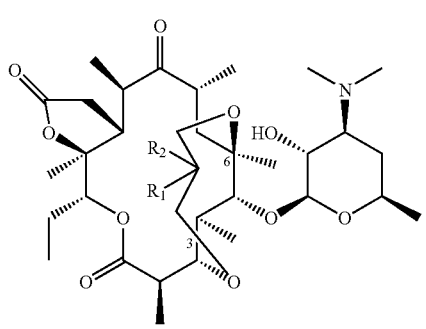

(A)

wherein $R_1$ and $R_2$ are delineated in Table 1 and Table 2.

Examples 8-179 are made from the title compound of Example 2 via similar method delineated in U.S. application Ser. No. 11/008,581.

In examples where a mixture of isomers is present may be separated by crystallization or HPLC.

Examples (180)-(341) of the Formula B

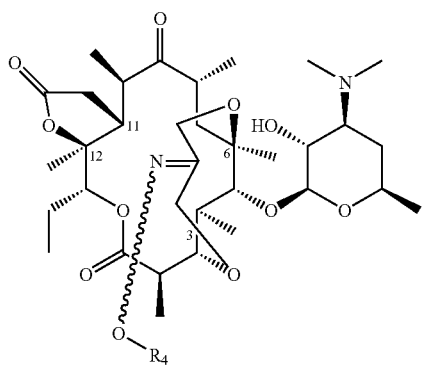

(B)

wherein $R_4$ is delineated for each example in Table 3.

Examples 180-341 are made from the title compound of Example 6 and the appropriate hydroxylamine of formula $R_4$—O—$NH_2$ via similar method delineated in PCT Application WO 03/097659 A1 and US Application US 2004/0157787 A1.

In all of the following examples a mixture of E and Z isomers are present which may be separated by crystallization or HPLC.

The substituted hydroxylamines used in the following examples are either commercially available or can be made according to PCT Application WO 03/097659 A1 and US Application US 2004/0157787 A1.

Examples 342-363 of the Formula D

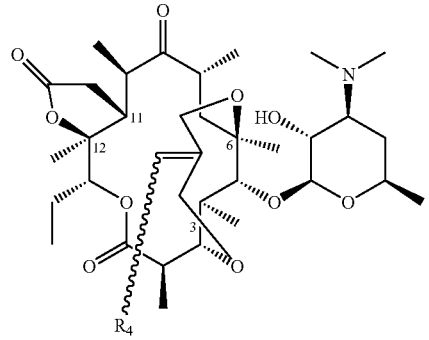

(D)

wherein $R_4$ is delineated for each example in Table 2.

Examples 342-363 are made from the title compound of Example 3 and the appropriate bromo compound of formula $R_4$-Br, wherein $R_4$ is as previously defined via similar method delineated in PCT Application WO 03/097659 A1 and US Application US 2004/0157787 A1.

In all of the following examples a mixture of E and Z isomers are present which may be separated by crystallization or HPLC.

The bromo compounds used in the following examples are either commercially available or can be made according to PCT Application WO 03/097659 A1 and US Application US 2004/0157787 A1.

Examples 364-405 of the Formula D

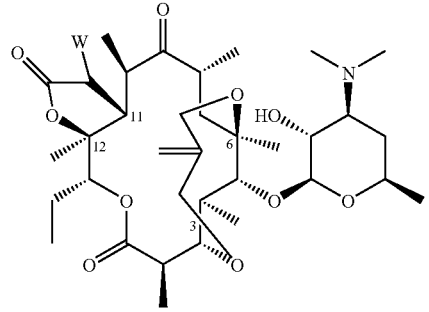

(D)

wherein W is delineated for each example in Table 3.

Examples 364-405 are made from the compound in Step 1 g of Example 1 via similar methods delineated in PCT Application WO 02/16380 A1, PCT Application WO 03/072588 A1, and PCT Application WO 2004/016634 A1.

In all of the following examples a mixture of diasteoreomers are present which may be separated by crystallization or HPLC.

The WH compounds used in the following examples are either commercially available or can be made according to PCT Application WO 02/16380 A1, PCT Application WO 03/072588 A1, and PCT Application WO 2004/016634 A1.

What is claimed:

1. A compound represented by formula (I):

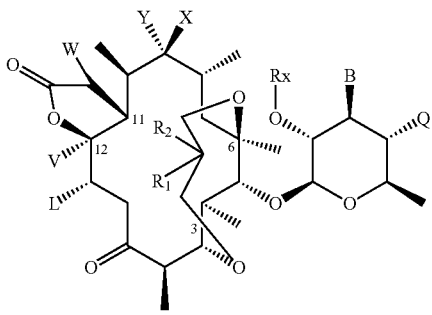

or the pharmaceutically acceptable salts, and esters thereof, wherein W is selected from the group consisting of:
a) hydrogen;
b) CN;
c) -E-$R_3$, where E is S, SO, $SO_2$, NH, $NCH_3$, $CH_2O$, $CH_2NH$, $CH_2NCH_3$ or CO; and $R_3$ is independently selected from the group consisting of:
  (i) —$C_1$-$C_6$ alkyl, —$C_2$-$C_6$ alkenyl, or —$C_2$-$C_6$ alkynyl; and
  (ii) —$C_1$-$C_6$ substituted alkyl, —$C_2$-$C_6$ substituted alkenyl, or —$C_2$-$C_6$ substituted alkynyl;
  provided that when A=S(O) or $SO_2$, $R_3$ cannot be hydrogen; and
$R_1$ is selected from the group consisting of:
a) hydrogen;
b) deuterium;
c) —$CH_2OH$;
d) aryl;
e) substituted aryl;
f) heteroaryl;
g) substituted heteroaryl; and
h) —$C_1$-$C_6$ alkyl, —$C_2$-$C_6$ alkenyl, or —$C_2$-$C_6$ alkynyl containing 0, 1, 2, or 3 heteroatoms selected from O, S or N, optionally substituted with one or more substituents selected from halogen, aryl, substituted aryl, heteroaryl, or substituted heteroaryl;
$R_2$ is:
a) hydrogen;
b) hydroxy; or
c) activated hydroxy;
when $R_1$ is H, $R_2$ is selected from the group consisting of:
a) hydrogen;
b) hydroxy;
c) activated hydroxy;
d) $N_3$;
e) $NH_2$;
f) CN;
g) protected hydroxy;
h) protected amino;
i) -A-$R_4$, where A is O, S, S(O), $SO_2$, NH, $NCH_3$, NH(CO), NH(CO)NH or $NHSO_2$; and $R_4$ is independently selected from the group consisting of:
  (i) hydrogen;
  (ii) aryl;
  (iii) substituted aryl;
  (iv) heteroaryl;
  (v) substituted heteroaryl;
  (vi) —$C_1$-$C_6$ alkyl, —$C_2$-$C_6$ alkenyl, or —$C_2$-$C_6$ alkynyl containing 0, 1, 2, or 3 heteroatoms selected from O, S or N, optionally substituted with one or more substituents selected from halogen, aryl, substituted aryl, heteroaryl, or substituted heteroaryl;
  (vii) —$C_3$-$C_{12}$ cycloalkyl containing 0, 1, 2, or 3 heteroatoms selected from O, S or N, optionally substituted with one or more substituents selected from halogen, aryl, substituted aryl, heteroaryl, or substituted heteroaryl;
  provided that when A=S(O) or $SO_2$, $R_4$ cannot be hydrogen; and

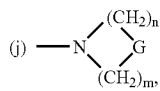

wherein G is absent, O, S, S(O), $S(O)_2$, $NR_4$, $N(CO)R_4$, $NSO_2R_4$, or $CHR_4$; n=1, 2, or 3; and m=2 or 3, where $R_3$ is as previously defined;
or alternatively, $R_1$ and $R_2$ taken together with the carbon atom to which they are attached is selected from the group consisting of:
a) C=O;
b) C($OR_5$)($OR_6$), where $R_5$ and $R_6$ are selected from the group consisting of C1-C12 alkyl, aryl or substituted aryl; or taken together are —$(CH_2)_m$—, and where m is 2 or 3;
c) C($SR_5$)($SR_6$), where $R_5$ and $R_6$ are as previously defined above;
d) C=$CHR_4$, where $R_4$ is as previously defined;
e) C=CNH; and
f) C=N-Z-$R_4$, where Z is absent, O, NH, NH(CO), NH(CO)NH or $NHSO_2$; and $R_3$ is as previously defined; and
X and Y are:
(a) when one of X and Y is a hydrogen, the other is selected from the group consisting of:
  (i) hydrogen;
  (ii) deuterium;
  (iii) hydroxy;
  (iv) protected hydroxy;
  (v) amino;
  (vi) protected amino; and

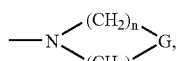

wherein G is absent, O, S, S(O), $S(O)_2$, $NR_4$, $N(CO)R_4$, $NSO_2R_4$, or $CHR_4$; n=1, 2, or 3; and m=2 or 3, where $R_4$ is as previously defined; or
b) X and Y taken together with the carbon atom to which they are attached is:
  (i) C=O;
  (ii) C=N—$OR_7$, wherein $R_7$ is selected from the group consisting of:
    1. hydrogen;
    2. —$CH_2O(CH_2)_2OCH_3$;
    3. —$CH_2O(CH_2O)_nCH_3$, wherein n is as previously defined;
    4. —$C_1$-$C_{12}$ alkyl, containing 0, 1, 2, or 3 heteroatoms, optionally substituted with one or more substituents selected from the group consisting of halogen, aryl, substituted aryl, heteroaryl and substituted heteroaryl;
5. $C_3$-$C_{12}$ cycloalkyl;
6. C(O)—$C_1$-$C_{12}$ alkyl;
7. C(O)—($C_3$-$C_{12}$ cycloalkyl);
8. C(O)—$R_4$, wherein $R_4$ is as previously defined; and
9. —Si($R_a$)($R_b$)($R_c$), wherein $R_a$, $R_b$ and $R_c$ are each independently selected from the group consisting of $C_1$-$C_{12}$ alkyl, aryl and substituted aryl; or (iii) C=N—O—C($R_8$)($R_9$)—O—$R_{10}$, wherein $R_8$ and $R_9$ taken together with the carbon atom to which they are attached form a $C_3$ to $C_{12}$ cycloalkyl group or each independently is selected from the group consisting of: hydrogen and $C_1$-$C_{12}$ alkyl; and $R_{10}$ is selected from the group consisting of:
  1. —$C_1$-$C_{12}$ alkyl, optionally substituted with one or more substituents selected from the group consisting of halogen, aryl, substituted aryl, heteroaryl and substituted heteroaryl;
  2. —$C_3$-$C_{12}$ cycloalkyl; and
  3. —Si($R_a$)($R_b$)($R_c$), wherein $R_a$, $R_b$ and $R_c$ are as previously defined;

B is $NR_{30}R_{40}$; wherein $R_{30}$ and $R_{40}$ is independently selected from the group consisting of hydrogen, acyl, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, saturated or unsaturated heterocyclic group; or can be taken together with the nitrogen atom to which they are attached to form a substituted or unsubstituted heterocyclic or heteroaromatic ring;

V is selected from the group consisting of hydrogen, azido, cyano, nitro, aldehyde, carboxylic acid, amide, a substituted or unsubstituted, saturated or unsaturated aliphatic;

Q is selected from the group consisting of:
  (a) hydrogen;
  (b) protected hydroxy; and
  (c) $OR_{11}$, where $R_{11}$ is a group consisting of:
    (i) hydrogen;
    (ii) aryl;
    (iii) substituted aryl;
    (iv) heteroaryl;
    (v) substituted heteroaryl;
    (vi) —$C_1$-$C_6$ alkyl, —$C_2$-$C_6$ alkenyl, or —$C_2$-$C_6$ alkynyl containing 0, 1, 2, or 3 heteroatoms selected from O, S or N, optionally substituted with one or more substituents selected from halogen, aryl, substituted aryl, heteroaryl, or substituted heteroaryl; and
    (vii) —$C_3$-$C_{12}$ cycloalkyl or —$C_3$-$C_{12}$ substituted cycloalkyl containing 0, 1, 2, or 3 heteroatoms selected from O, S or N, optionally substituted with one or more substituents selected from halogen, aryl, substituted aryl, heteroaryl, or substituted heteroaryl;

L is selected from the group consisting of:
  (a) —$CH_2CH_3$;
  (b) —CH(OH)$CH_3$; and
  (c) —$C_1$-$C_6$ alkyl, —$C_2$-$C_6$ alkenyl, or —$C_2$-$C_6$ alkynyl optionally substituted with one or more substituents selected from the group consisting of aryl, substituted aryl, heteroaryl, and substituted heteroaryl; and $R_x$ is hydrogen, hydroxyl protecting group or hydroxyl prodrug group.

2. A compound according to claim 1 represented by formula (II):

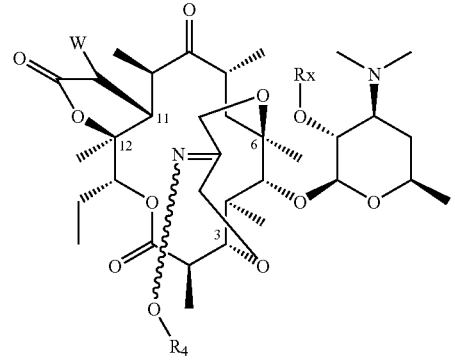

wherein W, $R_4$ and $R_x$ are as previously defined in claim 1.

3. A compound according to claim 1 represented by formula (III):

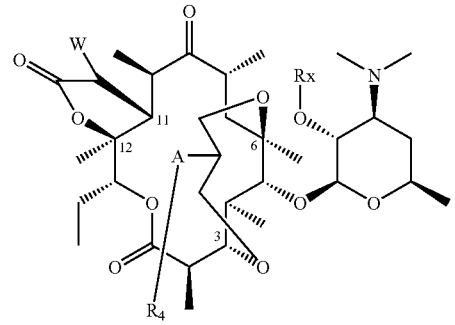

wherein W, $R_4$ and $R_x$ are as previously defined in claim 1.

4. A compound according to claim 1 represented by formula (IV):

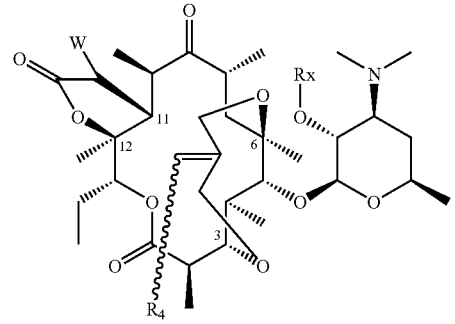

wherein W, $R_4$ and $R_x$ are as previously defined in claim 1.

5. A compound according to claim 1 represented by formula (V):

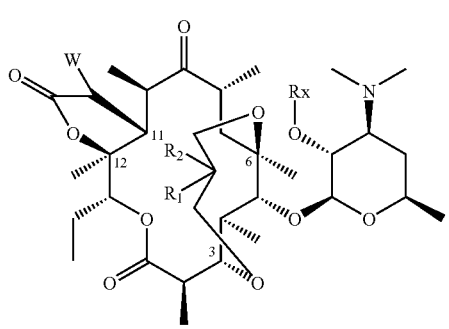

(V)

wherein W, $R_1$, $R_2$ and $R_x$ are as previously defined in claim 1.

6. A compound of claim 5, wherein $R_1$ and $R_2$ taken together with the carbon atom to which they are attached are C=$CH_2$, W=[—S($CH_2$)$_2$Ph] and Rx=Ac.

7. A compound of claim 5, wherein $R_1$ and $R_2$ taken together with the carbon atom to which they are attached are C=$CH_2$, W=[—S($CH_2$)$_2$Ph] and Rx=H.

8. A compound of claim 5, wherein $R_1$ and $R_2$ taken together with the carbon atom to which they are attached are C=$CH_2$, W=$CO_2$Me, and Rx=Ac.

9. A compound of claim 5, wherein $R_1$ and $R_2$ taken together with the carbon atom to which they are attached are C=$CH_2$, W=H and Rx=Ac.

10. A compound of claim 5, wherein $R_1$ and $R_2$ taken together with the carbon atom to which they are attached are C=$CH_2$, and W=Rx=H.

11. A compound of claim 5, wherein $R_1$ and $R_2$ taken together with the carbon atom to which they are attached are C=O, and W=Rx=H.

12. A compound of claim 5, wherein $R_1$ and $R_2$ taken together with the carbon atom to which they are attached are C=NO[6'-amino-[2,2']bipyridinyl-6-ylmethyl], W=Rx=H.

13. A compound of claim 1 having the Formula A, selected from compounds 8-179 of Table 1 and 2:

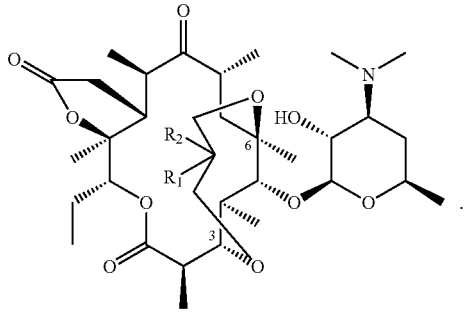

(A)

14. A compound of claim 1 having the Formula B, selected from compounds 180-341 of Table 3:

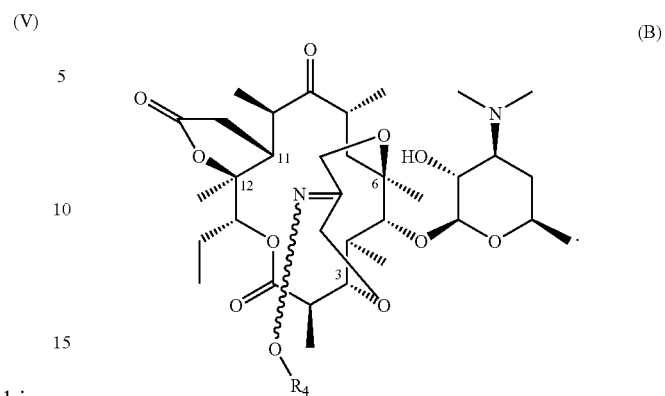

(B)

15. A compound of claim 1 having the Formula C, selected from compounds 342-363 of Table 4:

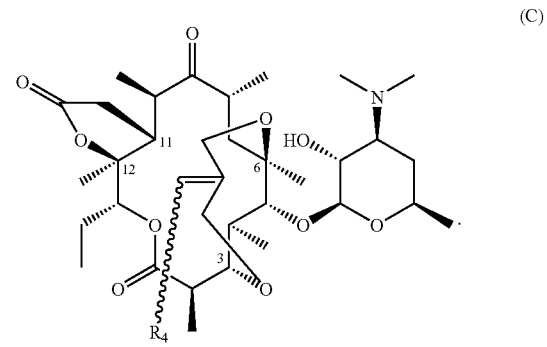

(C)

16. A compound of claim 1 having the Formula D, selected from compounds 364-405 of Table 5:

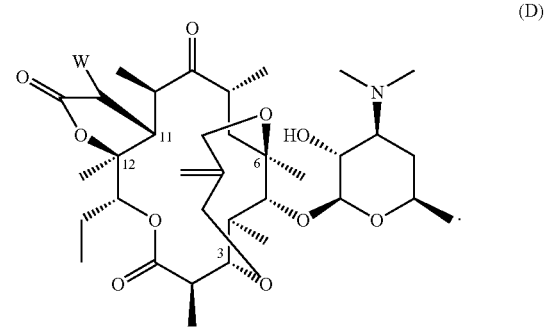

(D)

17. A method for treating a bacterial infection in a subject in need of such treatment, comprising administering to said subject a therapeutically effective amount of a compound according to claim 1.

18. A pharmaceutical composition comprising a therapeutically effective amount of a compound of claim 1 or a pharmaceutically acceptable salt, ester or prodrug thereof, in combination with a pharmaceutically acceptable carrier.

19. A method for treating a bacterial infection in a subject, comprising administering to said subject a therapeutically effective amount of a pharmaceutical composition according to claim 1.

20. A method of treating cystic fibrosis in a patient, comprising administering to said subject, therapeutically effective amount of a pharmaceutical composition of claim 18.

21. A method of treating inflammation in a subject comprising administering to said subject, therapeutically effective amount of a pharmaceutical composition of claim 18.

22. A process for preparing a compound of claim 1 having the formula

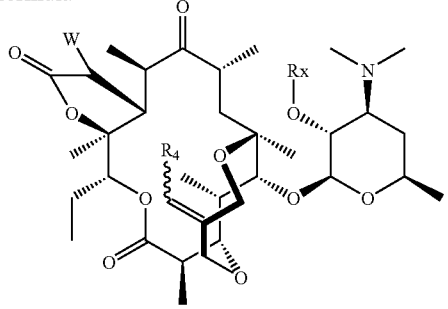

comprising the steps of:
(a) reacting a compound having a formula:

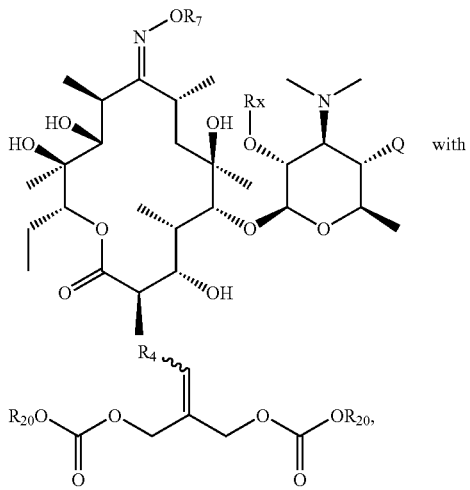

in the presence of a phosphine ligand and Pd(0) catalyst under room temperature to reflux conditions to prepare compounds of the formula:

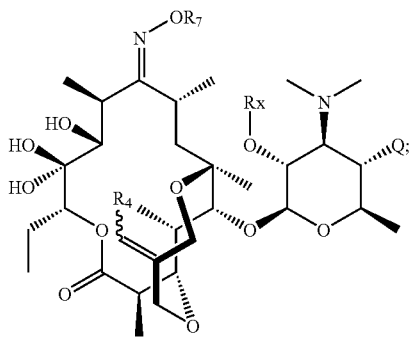

(b) deprotecting the 2' and the oxime groups of the compound obtained in step (a), followed by deoximating with an inorganic sulfur oxide salt or an inorganic nitrite salt in the presence to acid to form compound having a formula:

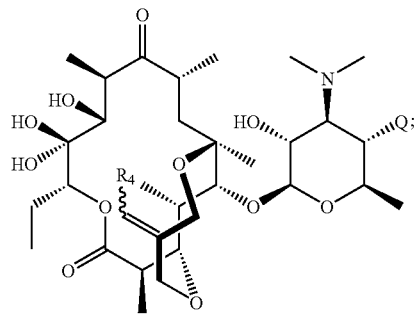

(c) protecting the 2' hydroxy of the compound from step (b) with a suitable hydroxy protecting group;

(d) treating the compound from step (c) with a base and a reagent selected from the group consisting of CDI, phosgene equivatents, isocysanates, chloroformates or ethylenecarbonate/Et$_3$N;

(e) treating compound from step (d) with appropriate carboxylic acid and coupling reagents in a suitable solvent; or alternatively, in a two-step procedure, treating compound from step (e) with chloroacetic acid, followed by appropriate nucleophile WH in the presence of base; and (f) treating compound from step (e) with an alkali metal in an aprotic solvent.

23. A process for preparing a compound of claim 2 comprising the steps of:

(a) oxidative cleavage of the compounds with the following formula:

103
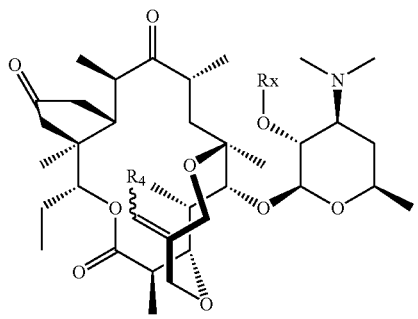
with oxidizing reagents to give a compound of the following formula:
104
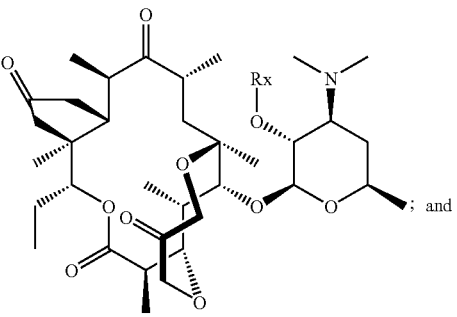
(b) reacting the compounds prepared in step (a) with $R_4ONH_2$ in a presence of a mild acid.
* * * * *